US008476252B2

(12) United States Patent
Achleitner et al.

(10) Patent No.: US 8,476,252 B2
(45) Date of Patent: *Jul. 2, 2013

(54) PHARMACEUTICAL EMULSION COMPOSITIONS COMPRISING PROGESTOGEN

(75) Inventors: Georg Achleitner, Graz (AT); Eva-Maria Hoiser, Hitzendorf (AT); Laura Pickersgill, Brussels (BE)

(73) Assignee: Besins Healthcare Luxembourg SARL, Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 13/093,612

(22) Filed: Apr. 25, 2011

(65) Prior Publication Data

US 2011/0262495 A1    Oct. 27, 2011

Related U.S. Application Data

(60) Provisional application No. 61/327,963, filed on Apr. 26, 2010, provisional application No. 61/327,968, filed on Apr. 26, 2010, provisional application No. 61/327,959, filed on Apr. 26, 2010, provisional application No. 61/424,411, filed on Dec. 17, 2010, provisional application No. 61/424,407, filed on Dec. 17, 2010, provisional application No. 61/424,402, filed on Dec. 17, 2010.

(30) Foreign Application Priority Data

| Apr. 26, 2010 | (EP) | 10161029 |
| Apr. 26, 2010 | (EP) | 10161032 |
| Apr. 26, 2010 | (EP) | 10161034 |
| Dec. 17, 2010 | (EP) | 10195760 |
| Dec. 17, 2010 | (EP) | 10195764 |
| Dec. 17, 2010 | (EP) | 10195766 |

(51) Int. Cl.
*A61K 31/56* (2006.01)
(52) U.S. Cl.
USPC ........................................ 514/177
(58) Field of Classification Search
USPC .................. 514/177, 938; 424/400
See application file for complete search history.

(56) References Cited

U.S. PATENT DOCUMENTS

| 6,720,001 B2 * | 4/2004 | Chen et al. ............ 424/455 |
| 2005/0238675 A1 | 10/2005 | Li et al. |
| 2011/0262494 A1 | 10/2011 | Achleitner et al. |

FOREIGN PATENT DOCUMENTS

| EP | 1 488 785 A1 | 12/2004 |
| EP | 1 611 879 A1 | 1/2006 |
| IL | 89856 A | 5/1993 |
| WO | WO 96/10991 A1 | 4/1996 |
| WO | WO 0107086 A1 * | 2/2001 |

OTHER PUBLICATIONS

International Search Report issued on Dec. 13, 2011 in application No. PCT/EP2011/056548 (corresponding to US 2011/0262494).
International Search Report issued on Dec. 13, 2011 in application No. PCT/EP2011/056539.
Database Caplus [Online] Chemical Abstracts Service, Columbus, Ohio, US; Apr. 2, 2008, Zhang et al., "Pharmaceutical emulsions for injection containing progesterone," XP002599890, retrieved from STN Database accession No. 2008:429757, abstract.
Database WPI, Week 198606, Thomson Scientific, London, GB; AN 1986-038601, XP002207311, "Progesterone-emulsified intravenous injection—of progesterone, vegetable oil, lecithin and opt. benzylbenzoate" & JP 60 258110 (Daigo Eiyo Kagaku KK), Dec. 20, 1985.

* cited by examiner

*Primary Examiner* — Frederick Krass
*Assistant Examiner* — Dennis J Parad
(74) *Attorney, Agent, or Firm* — Foley & Lardner LLP

(57) ABSTRACT

Described are a sterile, ready-to-use, pharmaceutical oil-in water emulsion compositions for parenteral administration comprising:
  0.015 to 1.2% wt/vol of progestogen;
  0.5-30% wt/vol oil, wherein the oil comprises at least 85% wt/wt triglyceride;
  0.0425-12.5% wt/vol phospholipid;
  61.4-99.4% wt/vol aqueous medium;
wherein the phospholipid is present in an amount of 6.8%-43% of the oil (wt/wt), and wherein the progestogen is present in an amount greater than or equal to 2.1 wt % of the oil.
Also described are methods of making such compositions and method of using such compositions in therapeutic or prophylactic treatment, such as treatments comprising intravenous administration of the pharmaceutical composition.

20 Claims, No Drawings

PHARMACEUTICAL EMULSION COMPOSITIONS COMPRISING PROGESTOGEN

CROSS REFERENCE TO RELATED APPLICATIONS

This application claims priority under 35 U.S.C. §119(e) to U.S. provisional application Ser. No. 61/327,968, filed Apr. 26, 2010, U.S. provisional application Ser. No. 61/327,959, filed Apr. 26, 2010, U.S. provisional application Ser. No. 61/327,963, filed Apr. 26, 2010, U.S. provisional application Ser. No. 61/424,407, filed Dec. 17, 2010, U.S. provisional application Ser. No. 61/424,402, filed Dec. 17, 2010, U.S. provisional application Ser. No. 61/424,411, filed Dec. 17, 2010, and under 35 U.S.C. §119(a) to European application serial number 10161029.3, filed Apr. 26, 2010, European application serial number 10161032.7, filed Apr. 26, 2010, European application serial number 10161034.3, filed Apr. 26, 2010, European application serial number 10195766.0, filed Dec. 17, 2010, European application serial number 10195764.5, filed Dec. 17, 2010, and European application serial number 10195760.3, filed Dec. 17, 2010, all of which are incorporated herein by reference in their entirety.

FIELD OF THE INVENTION

The invention relates to pharmaceutical compositions comprising a progestogen, and to therapeutic or prophylactic treatment of mammals comprising parenteral administration of such a pharmaceutical composition. The compositions are particularly suitable for treating a traumatic injury to the central nervous system.

BACKGROUND

Traumatic Brain Injury (TBI) is a non-degenerative, non-congenital insult to the brain from an external mechanical force, possibly leading to permanent or temporary impairments of cognitive, physical and psychosocial functions with an associated diminished or altered state of consciousness (Brown, A. W., et. al., 2008, Arch. Phys. Med. Rehabil., 89 (Supp. 1), S3-8). TBI is a major cause of death and disability worldwide. It is estimated that more than 1.5 million Americans sustain a TBI each year, and the incidence of TBI in other industrialized countries is comparable to the U.S. (Traumatic Brain Injury: Methods for Clinical and Forensic Neuropsychiatric Assessment, p. 2, Granacher, ed., CRC Press 2003). For example, in Europe there are approximately 66,000 deaths annually attributed to Till (Socin, D. M., et al. (1995). JAMA 273(22), 1778-80). Some patients have a long-term or lifelong need for help to perform activities of daily living as a result of TBI.

Despite the enormity of the problem posed by TBI, there are currently no approved medications proven to be effective in improving mortality or in improving outcomes following TBI. However, two recent clinical trials have demonstrated successful treatment of TBI with the steroid hormone progesterone (Xiao et al, 2008, Crit. Care, 12: R61; Wright et al Ann. Emerg. Med. 2007, 49: 391-402). Both studies showed that progesterone is safe and well tolerated in TBI patients, and that administration of progesterone to TBI patients leads to decreased mortality. Furthermore, patent applications WO2006/102644, WO2006102596, and WO2008/039898 outline methods for treatment of TBI by parenterally administering progestogen.

The most effective route of administration of progestogens such as progesterone is via parenteral, or intravenous administration. However, the hydrophobic nature of the progesterone molecule, and hence its poor solubility in water, presents formulation limitations. Aqueous solutions do not offer formulations capable of delivering effective therapeutic doses of progesterone to patients. However, progesterone is sufficiently lipophilic to enable therapeutically effective concentrations to be prepared in hydrophobic solvents, such as triglyceride based solvents.

The delivery of hydrophobic drugs via intravenous infusion of oil-in-water emulsions is known in the art. Examples include Taxol® and Abraxane®, which are nanoformulations of the chemotherapy drug paclitaxel designed for intravenous administration, and Diprivan®, which is a lipid emulsion formulation of the anaesthetic propofol marketed by APP pharmaceuticals, IL, USA. Intravenous administration of progesterone with an oil-in-water emulsion has also been previously described (Wright D W et al. supra; Trotter et al, Journal of Clin. Endocrinol. & Metab. (1999) Vol. 84, page 4531).

The ProTECT study (Wright et al., Ann. Emerg. Med. 2007, 49: 391-402) utilized a 2-component system, wherein progesterone is firstly dissolved in an alcoholic solution (first component), and this alcoholic progesterone solution is subsequently injected into the commercially available lipid emulsion Intralipid® 20% (Fresenius Kabi, Sweden) (second component), and manually mixed (such as by shaking) shortly before intravenous administration of the alcoholic solution/emulsion mixture. There are multiple disadvantages of using this method of preparation:

Firstly, administration of alcoholic solutions to TBI patients is not desirable. Secondly, whilst the presence of alcohol aids solubilisation of the progesterone, low shear manual mixing does not enable all of the progesterone to enter the oil phase. Consequently such emulsions are capable of solubilising only a limited amount of progesterone, and large amounts of lipid must therefore be administered in order to achieve the desired serum-progesterone levels. However, administration of large volumes of emulsion, and/or large amounts of lipid to the patient can have serious consequences, such as induction of hyperlipidemia or oedema. The patient is, as a result, exposed to an undesirable lipid and/or liquid load and is placed at risk of adverse reactions.

Furthermore, non-dissolved progesterone is susceptible to crystallisation, and subsequently oxidation in the aqueous phase, thus causing not only elevated levels of particulate matter to accumulate in the composition, but also high levels of degradation products of the active ingredient. Indeed, it has been shown that, when an alcoholic solution of progesterone is injected into a commercial lipid emulsion composition (such as Intralipid® 20%), a fraction of the hormone is found in crystalline form rather than becoming solubilised in the emulsion. This non-solubilized progesterone has been reported to be adsorbed at the surface of the infusion bags and feed ducts. The observation that not all of the progesterone enters the oil phase of these 2-component emulsions leads to uncertainty as to the concentration of progesterone achieved in the final composition, and the bio-availability of the hormone.

Finally, due to stability issues, the progesterone-lipid mixture of 2-component systems must be prepared only hours ahead of administration (i.e. the first component is added to the second component and mixed within hours of use), as the resulting mixture may not be stored at room temperature. It is both time consuming and inconvenient for medical practitioners to prepare such mixtures on demand, and particularly unsatisfactory in the context of TBI therapy, where prompt treatment can be important to patient outcome.

Alternative methods for making hormone-containing emulsions describe the incorporation of hormone directly into the oil during manufacture of the lipid emulsion.

WO 96/10991 describes pharmaceutical compositions for transmucosal administration of estradiol in combination with a progestin.

WO 01/28555 describes oil-in-water emulsion systems for the delivery of polyfunctional active ingredients. The emulsions comprise, in addition to an active ingredient, polarity modifiers, said to be capable of modifying the interaction between the polyfunctional active ingredient and the oil phase, by serving as a bridge to reduce the effects of the gap in polarity between the active ingredient and the oil.

US 2007/0071777 describes a method of making a 20% lipid emulsion comprising progesterone, which serves as a stock solution that is used to prepare (by dilution) a 5% lipid emulsion.

CN 101152186 describes the use of the surfactants Solutol S15 or poloxamer 188 in the preparation of injectable progesterone formulations. Whilst use of these surfactants may achieve a high progesterone solubility, intravenous administration of high concentrations of these surfactants is associated with undesirable side-effects including moderate elevation in histamine release, urticaria, and anaphylactic reactions (pruritis, erythema).

One method of increasing the solubility of progesterone in lipid emulsions known in the art is the use of organic solvents. Progesterone is highly soluble in benzoic acid or its derivatives. For example, JP 60-258110 describes the use of benzyl benzoate to increase progesterone solubility in an oil emulsion. However, since benzyl alcohols and benzyl benzoate are commonly toxic and are known to elicit allergies, their inclusion in compositions for parenteral administration is considered a serious danger.

There remains a need, therefore, for physically stable formulations of progestogen suitable for parenteral, particularly intravenous, administration.

SUMMARY

In accordance with some embodiments, the present invention provides pharmaceutical compositions comprising progestogen, wherein said compositions are in the form of an emulsion comprising an aqueous phase, an oil phase, and a surfactant.

In accordance with some embodiments, there are provided sterile, ready-to-use, pharmaceutical oil-in water emulsion compositions for parenteral administration comprising:
  0.015 to 1.2% wt/vol progestogen;
  0.5-30% wt/vol oil wherein the oil comprises at least 85% wt/wt triglyceride;
  0.0425-12.5% wt/vol phospholipid;
  61.4-99.4% wt/vol aqueous medium;
  wherein the phospholipid is present in an amount of 6.8%-43% of the oil (wt/wt), and wherein the progestogen is present in an amount greater than or equal to 2.1% wt/wt of the oil, or greater than or equal to 2.2% wt/wt of the oil.

In specific embodiments, the composition contains less than 2.5% wt/vol benzyl benzoate, or less than 1% wt/vol benzyl benzoate. In specific embodiments, the phospholipid is present in an amount within the range of 8.4-42.5% wt/wt of the oil, or 12-26% wt/wt of the oil, or 15-22% wt/wt of the oil. In specific embodiments, the progestogen is present in an amount greater than 2.5% or greater than 3% wt/wt of the oil.

In specific embodiments, the composition contains 0.005-10 wt % of a co-surfactant, such as oleate, oleic acid and combinations thereof, which may be present in the range of 0.005-2.5 wt %. In specific embodiments, the progestogen is progesterone.

In specific embodiments, the composition contains an osmotic agent, such as glycerol. In specific embodiments, the composition is suitable for intravenous administration. In specific embodiments, the composition has an osmolality of between 200 and 1000 mOsm/kg, or between 220 and 600 mOsm/kg, or between 230 to 360 mOsm/kg. In specific embodiments, the composition has a $PFAT_5$ value of $\leq 0.05\%$. In specific embodiments, the droplet particles of the dispersed oil phase of the composition have a volume-based mean diameter of $\leq 300$ nm, or $\leq 250$ nm, or $\leq 200$ nm, or $\leq 185$ nm, or $\leq 80$ nm.

In accordance with other embodiments, there are provided methods of treatment comprising administering a composition as described herein to a subject in need thereof. In specific embodiments, the subject is human. In specific embodiments, the subject suffers from a traumatic central nervous system injury.

In accordance with other embodiments, there are provided methods of manufacturing a composition according to claim 1, comprising (a) combining water, phospholipid and, optionally, an osmotic agent, to produce an aqueous composition; (b) combining progestogen and oil to produce an oily composition; and (c) combining the aqueous composition and the oily composition, followed by homogenization to form a homogenous oil-in-water emulsion. In specific embodiments, step (c) comprises adding the oily composition to the aqueous composition, and homogenization at greater than or equal to 350 bar.

DETAILED DESCRIPTION

The present invention provides pharmaceutical compositions comprising progestogen, wherein said compositions are in the form of an emulsion comprising an aqueous phase, an oil phase, and a surfactant.

One embodiment, referred to herein as the "Phospholipid/Oil embodiment," provides a pharmaceutical oil-in-water emulsion composition for parenteral administration comprising:
  0.015 to 1.2% wt/vol of progestogen;
  0.5-30% wt/vol of oil, wherein the oil comprises at least 85% wt/wt triglyceride;
  0.0425-12.5% wt/vol of phospholipid;
  61.4 to 99.4% wt/vol aqueous medium;
wherein the phospholipid is present in an amount of 6.8% to 43% of the oil (wt/wt), and wherein the progestogen is present in an amount greater than or equal to 2.1% wt/wt of the oil, including greater than or equal to 2.2% wt/wt of the oil. The composition may be provided as a sterile, ready-to-use composition.

Another embodiment, referred to herein as the "Progestogen/Oil embodiment," provides a pharmaceutical, oil-in-water emulsion composition for parenteral administration comprising:
  an oil;
  an aqueous phase; and
  a progestogen, such as progesterone;
wherein the progestogen:oil wt/wt ratio is at least 1:32, and wherein the composition contains less than 2.5% wt/vol benzyl benzoate, and optionally contains less than 1.5% wt/wt polyethylene glycol 15-hydroxystearate. The composition may be provided as a sterile, ready-to-use composition.

The present invention addresses problems in the art of formulating emulsions in general, and emulsions comprising a progestogen in particular. For example, under most conditions emulsions are thermodynamically unstable, since droplets spontaneously agglomerate, eventually leading to complete phase separation. The tendency for agglomeration and phase separation presents problems of storage and handling, and increases the likelihood that pharmaceutical emulsions initially properly prepared will be in a less optimal, less effective and poorly-characterized state upon ultimate administration to a patient. The presence of hydrophobic active agents in the emulsion, such as progesterone, further exacerbates these problems since the drug itself destabilizes the emulsion. It can be difficult therefore, to formulate heat-sterilizable, and storage-stable emulsions capable of delivering high enough doses of progestogen to be therapeutically useful, whilst also being safe to administer parenterally, especially intravenously.

The present invention addresses and overcomes many of these problems, however, and provides stable pharmaceutical emulsion compositions comprising progestogen, which are suitable for parenteral administration. In specific embodiments, such compositions exhibit one or more beneficial characteristics such as having an improved safety profile, being heat-sterilizable, and having improved storage stability, for example, such as being able to be provided in a ready-to-use form and stored for prolonged periods prior to use.

In accordance with other embodiments, the invention provides improved pharmaceutical emulsion compositions suitable for parenteral administration that are capable of delivering high doses of progestogen per unit oil administered.

Additionally or alternatively, in accordance with some embodiments, the invention provides cost-effective compositions for the safe, effective and convenient parenteral administration of progestogen to subjects. In more specific aspects of these embodiments, the invention provides compositions for parenteral administration which provide an improved availability of the progestogen contained therein (e.g. good pharmacokinetics and bioavailability, such as may be reflected in serum hormone levels and/or plasma concentration), whilst exposing the subject to which the composition is administered to a lower oil and/or lower volume load than compositions of the prior art.

The compositions are suitable for parenteral, including intravenous, administration. Accordingly, the use of the compositions described herein for parenteral administration is another aspect of the invention. Additionally, the invention provides methods for treating a traumatic CNS injury, such as a traumatic brain injury (TBI), by administering to a subject said progestogen compositions in a therapeutically effective amount. The treatment of other CNS disorders and the relief of their symptoms is also contemplated, as discussed further herein below.

The invention further provides processes for the preparation of the compositions described herein.

DEFINITIONS

The term "oil" as used herein is readily interchangeable with "lipid" and "fat", and refers to lipophilic high-boiling organic compounds that are liquid at body temperatures, (e.g. about 37° C.), and are pharmacologically acceptable in injectable formulations. The oils of the present invention encompass both glycerides, partial glycerides, fatty acid residues and non-glycerides (e.g. cholesterol), as well as mixtures thereof. Phospholipids, unless otherwise indicated, are not encompassed by the term "oil" as used herein.

The term "oil-in-water emulsion" as used herein, refers to a colloidal dispersion system in which liquid oil is dispersed in small droplets (the discrete phase) in an aqueous medium (the continuous phase).

The term "phospholipid" as used herein refers an ester of glycerol with one or two fatty acids and one phosphate ion. In addition to glycerol-derived phospholipids, the term "phospholipid" as used herein also encompasses sphingomyelin.

The term "aqueous medium" as used herein refers to a water-containing liquid.

The term "low-oil" as used herein refers to compositions having a total oil content wt/vol of less than or equal to 10%.

The term "high-oil" as used herein refers to compositions having a total oil content wt/vol of greater than 10%.

As used herein, the singular forms "a," "an," and "the" designate both the singular and the plural, unless expressly stated to designate the singular only.

As used herein, the phrase "therapeutically effective amount" means that drug dosage that provides the specific pharmacological response for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

Unless indicated otherwise, whenever reference is made herein to "percentage weight per volume" or "% wt/vol" these terms describe the mass of the component in g per 100 mL of the composition in which it is contained. Unless indicated otherwise, whenever reference is made herein to "percentage weight per weight" or "% wt/wt" these terms denote the mass of a component as a percentage of the mass of the composition in which the component is contained.

When "volume-weighted percentage fat>5 µm", or "$PFAT_5$" is referred to herein, what is meant is volume-weighted percentage of dispersed fat having a diameter of more than 5 µm measured according to the method described in USP, chapter <729>, Method II, using the Accusizer (780 Automatic Particle Sizer).

Whenever "PCS" or "Photon Correlation Spectroscopy" is referred to herein, what is meant is PCS as measured according to the method described in USP, Chapter <729>, Method I, using the Zetasizer 1000 HSA (Malvern Instruments).

Whenever "D[4,3]" (volume-based median diameter) or d(0,5) (volume-based mean diameter) is referred to herein, what is meant is D[4,3] or d(0,5), measured according to the method described in USP <429> (Light diffraction measurement of particle size), using the Mastersizer 2000 with Hydro S dispersion unit (Malvern Instruments).

Whenever "zeta-potential" is referred to herein, what is meant is the electrokinetic potential in colloidal systems as determined experimentally using Zetasizer 1000 HAS (Malvern Instruments).

Whenever the term "free of crystalline solid" is used herein, it is meant that emulsions of the present invention meet the standards for particulate size and count in injection liquids (USP 788, Method 2—Microscopic Particle count test).

Components of the Compositions

1. Progestogen

The compositions of the present invention comprise a progestogen as an active pharmaceutical ingredient (API). As used herein, "progestogen" include both natural progesterone and synthetic progestogens. In general, the progestogens have the general Formula I, wherein $X_1$ and $X_2$ are independently selected from $COCH_3$, $OCOC_5H_{11}$, OH, C≡CH, $OCOCH_3$, H, $CH_2C$≡N; wherein $X_3$ is selected from H, $CH_3$, or Cl; wherein $X_4$ is selected from H, OH, or $CH_3$; and wherein $X_5$ is selected from $CH_3$ or $CH_2CH_3$ The progestogen may contain ring structures with one of more double bonds, for example between carbons 3 and 4, 4 and 5, 5 and 6, 6 and 7, 5 and 10, 10 and 9, and/or 15 and 16.

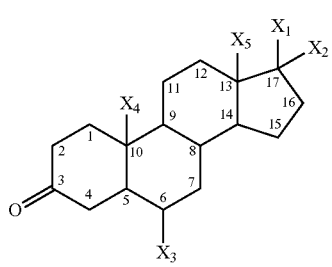

Formula I

Such progestogens include, for example, derivatives of progesterone such as 5-α-dihydroprogesterone, 6-dehydro-retroprogesterone (dydrogesterone), hydroxyprogesterone caproate, levonorgestrel, norethindrone, norethindrone acetate; norethynodrel, norgestrel, medroxyprogesterone, chlormadinone, and megestrol. "rogestogen" also includes, but is not limited to, modifications that produce 17α-OH esters of progesterone, as well as, modifications that introduce 6-α-methyl, 6-methyl, 6-ene, and 6-chloro substituents onto progesterone, and/or 19-norprogesterones. Further, non-limiting examples, of synthetic progestogens include, norethindrone (Micronor®), norgestrel (Ovrette®), levonorgestrel (Norplant®; with ethinyl estradiol; Alesse®, Nordette®), gestodene, medroxyprogesterone acetate (Provera®), promegestone, nomegestrol acetate, lynestrenol and dienogest.

In one embodiment, the progestogen is selected from the group consisting of progesterone, norethynodrel, norethidrone acetate, medroxyprogesterone, medroxyprogesteron 17-acetate, levonorgestrel, dydrogesterone, hydroxyprogesterone caproate, norethidrone, gestodene, nomegestrol acetate, promegestone, dienogest, chlormadinion, megestrol, megestrol acetate, and/or mixtures thereof.

In one embodiment the progestogen is selected from the group consisting of 5-alpha-dihydroprogesterone, medroxyprogesterone, dydrogesterone, and progesterone and/or mixtures thereof.

In specific embodiments, the progestogen is progesterone. The term "progesterone" as used herein refers to a member of the progestogen family having the structure of Formula II below:

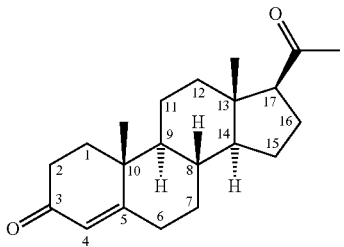

Formula II

Progesterone is also known as D4-pregnene-3,20-dione; delta-4-pregnene-3,20-dione; or pregn-4-ene-3,20-dione. In very specific embodiments, the progesterone is micronized. Proquina (Mexico) is one supplier of micronized progesterone.

The progestogen suitable for use in accordance with the present invention may be in the form of a pharmaceutically acceptable salt.

The compositions according to the "Progestogen/Oil embodiment" suitably comprise an amount of progestogen of at least 0.015% and not more than 1.2% wt/vol In specific embodiments, the compositions according to both the "Phospholipid/Oil embodiment" and the "Progestogen/Oil embodiment" comprise an amount of progestogen of at least 0.05%, at least 0.1%, at least 0.13%, or at least 0.16% weight per total volume (wt/vol). In accordance with any of these embodiments, the compositions may comprise an amount of progestogen less than or equal to 1.0%, less than or equal to 0.95%, less than or equal to 0.63%, less than or equal to 0.5%, or less than or equal to 0.4% weight per total volume (wt/vol). In other embodiments, the compositions may comprise an amount of progestogen less than or equal to 0.3% weight per total volume (wt/vol). In specific embodiments, the compositions invention comprise 0.2% weight per total volume of progesterone, which may be micronized progesterone.

Other Pharmaceutically Active Ingredients

The compositions according to the present invention may comprise one or more further therapeutic ingredients (APIs), such as other neurotrophic and/or neuroprotective agents. Such agents include, for example, compounds that reduce glutamate excitotoxicity and enhance neuronal regeneration. Such agents may be selected from, but are not limited to, the group comprising growth factors. By "growth factor" is meant an extracellular signaling molecule that stimulates a cell to grow or proliferate.

In other embodiments, the compositions comprise other APIs for other therapeutic effects. In one embodiment, the compositions of the present invention comprise Vitamin D. For example, the compositions may comprise Vitamin D in an amount sufficient to provide a dose of about 200 to 1000 IU per day, such as for example about 0.1 to 5 IU/ml, including about 0.5 to 3 IU/ml.

In other embodiments the compositions of the present invention do not contain any further APIs. In a specific aspect of these embodiments, the composition does not contain estradiol, more specifically they do not comprise estrogen.

2. Oil Phase

As discussed above, the compositions of the present invention are oil-in-water emulsions. The oil (hydrophobic) phase comprises an oil.

Triglycerides are exemplary oils for use in the compositions described herein. For example, the hydrophobic/oil phase may comprise a triglyceride that has a melting point of less than 30° C., more specifically of less than 20° C., including less than 10° C.

The compositions according to the "Progestogen/Oil embodiment" suitably contain oil comprising at least 75% wt/wt triglycerides, including at least 85% wt/wt triglycerides.

In specific embodiments of both the "Phospholipid/Oil embodiment" and the "Progestogen/Oil embodiment" the hydrophobic phase is an oil comprising at least 90% wt/wt triglycerides, including at least 95% wt/wt triglycerides. In more specific embodiments, the oil phase comprises "long-chain triglycerides" (LCT) in an amount of at least 45% wt/wt of the total oil, at least 65% wt/wt, at least 75% wt/wt, or at least 90% wt/wt.

In certain embodiments the oil is or comprises a vegetable oil. "Vegetable oil" refers to oil derived from plant seeds or nuts. Vegetable oils are typically "long-chain triglycerides" (LCT), formed when three fatty acids (usually about 14 to about 22 carbons in length, with unsaturated bonds in varying numbers and locations, depending on the source of the oil) form ester bonds with the three hydroxyl groups on glycerol. In certain embodiments, vegetable oils of highly purified grade (also called "super refined") are used to ensure safety and stability of the oil-in-water emulsions. In certain embodiments hydrogenated vegetable oils, which are produced by controlled hydrogenation of the vegetable oil, may be used.

Exemplary vegetable oils include but are not limited to almond oil, babassu oil, black currant seed oil, borage oil, canola oil, caster oil, coconut oil, corn oil, cottonseed oil, olive oil, peanut oil, palm oil, palm kernel oil, rapeseed oil, safflower oil, soybean oil, sunflower oil and sesame oil. Hydrogenated and/or or partially hydrogenated forms of these oils may also be used. In specific embodiments, the oil is or comprises safflower oil, sesame oil, corn oil, olive oil and/or soybean oil. In more specific embodiments, the oil is or comprises safflower oil, and/or soybean oil.

In specific embodiments where the oil is soy bean oil, the soybean oil may have a palmitic acid content (wt/wt) of between 9 and 13%, a stearic acid content of between 2.5% and 5%, an oleic acid content of between 17% and 30%, a linoleic acid content of between 48% and 58%, and a linolenic acid content of between 5% and 11%.

In a specific embodiment the emulsion compositions comprise no more than 3% wt/wt, including less than 2% wt/wt, or less than 1% wt/wt of structured triglycerides. A "structured triglyceride" as used herein is a triglyceride comprising triglycerides or mixtures of triglycerides having at least one fatty acid group with a carbon chain length of from 6 to 12 carbon atoms and at least one fatty acid group with a carbon chain length of more than 12 carbon units.

In another embodiment, the emulsion compositions comprise structured triglyceride in an amount expressed as % wt/wt of the total oil, of no more than 30%, including no more than 20%, no more than 10%, and no more than 5%.

In certain embodiments, the oil of the oil-in-water emulsion compositions described herein may additionally or alternatively comprise medium chain triglycerides. "Medium chain triglycerides" (MCTs) are another class of triglyceride oil that can be either naturally derived or synthetic. MCTs are formed from fatty acids of 6 to 10 carbons in length. MCTs are used extensively in emulsions for injection as a source of calories. Such an oil is commercially available as for example Miglyol 812 (SASOL GmbH Germany), or CRODAMOL GTCC-PN (Croda Inc, New Jersey). Other low-melting medium chain oils may also be used in the present invention. In certain embodiments combinations of vegetable oil and MCT oil are used in the present invention. In specific embodiments, the oil used in the compositions comprises less than or equal to 35% (wt/wt) medium chain triglycerides (MCT), less than or equal to 25% (wt/wt) MCT, less than or equal to 10% (wt/wt) MCT, or less than or equal to 5% (wt/wt) MCT.

In another embodiment, the oil phase comprises animal fat. "Animal fat" refers to oil derived from an animal source. Animal fat also comprises triglycerides, but the lengths of, and unsaturated bonds in, the three fatty acid chains vary compared to vegetable oils. Animal fats from sources that are solid at room temperature can be processed to render them liquid if desired. Other types of animal fats that are inherently liquid at room temperature include marine oils, such as fish oils. Fish oil triglycerides usually have fatty acids having from 12 to 22 carbon atoms. Exemplary fish oils include, for example, highly purified fish oil concentrates.

In certain embodiments the oil of the oil phase is a mixture of one or more of a LCT oil and/or an MCT oil and/or an oil of marine origin. Whilst MCTs reportedly enable better solubilisation of active ingredients compared to the less polar long chain triglycerides, the presence of predominantly MCTs in emulsions for injection is associated with adverse metabolic effects, and thus may raise safety and stability issues. Furthermore, hydrolysis products of MCTs, such as caprylic acid esters, are known to have detrimental neurological side effects. In specific embodiments, the compositions therefore comprise no more than 3% wt/wt MCT, no more than 2% wt/wt MCT, or no more than 1% wt/wt MCT. For example, in specific embodiments, the compositions do not contain MCT oils.

In a specific embodiment, the emulsion contains no more than 0.9% wt/wt, including no more than 0.8% wt/wt, or no more than 0.5% wt/wt, of a polarity modifier selected from the group consisting of monoglycerides, diglycerides, acetylated monoglycerides, acetylated diglycerides, and/or mixtures thereof. In another specific embodiment, the emulsion contains no more than 0.9% wt/wt, including no more than 0.8% wt/wt, such as no more than 0.5% wt/wt monoglyceride.

Expressed differently, in specific embodiments the emulsion contains not more than 30%, including not more than 20%, not more than 10%, or not more than 5% by weight of phospholipid, of a polarity modifier selected from the group consisting of monoglycerides, diglycerides, acetylated monoglycerides, acetylated diglycerides and/or mixtures thereof. The use of a polarity modifier in a significant concentration relative to the phospholipid content of the emulsions may have an adverse effect on the stabilizing properties of the phospholipid.

In another embodiment, the compositions comprise a polarity modifier selected from the group consisting of monoglycerides, diglycerides, acetylated monoglycerides, acetylated diglycerides and/or mixtures thereof, in an amount expressed as % wt/wt of the total oil, of less than 20%, including less than 10%, less than 5%, or less than 2%. In another embodiment the oil phase comprises less than or equal to 10% wt/wt of the total oil monoglycerides and/or acetylated monoglycerides.

The total oil content (wt/vol) of the compositions according to the "Progestogen/Oil embodiment" may be is at least 0.5% and not more than 30% (wt/vol).

The total oil content of the compositions according to both the "Phospholipid/Oil embodiment" and the "Progestogen/Oil embodiment" may be at least 1% (wt/vol), at least 2% (wt/vol), at least 4% (wt/vol), or at least 5% (wt/vol). In accordance with any of these embodiments, the total oil component of the compositions may be less than or equal to 29%

(wt/vol), less than or equal to 20% (wt/vol), less than or equal to 15% (wt/vol), or less than or equal to 10% (wt/vol). In specific embodiments, the total oil component is less than or equal to 9% (wt/vol).

In specific embodiments, the compositions comprise 6% wt/vol oil, such as soy bean oil. Exemplary soybean oils may have a linoleic acid content of greater than 48%, and an oleic acid content of greater than 17%. An example of a soybean oil having these properties is refined Soya-bean oil by Fresenius Kabi (Sweden).

In certain embodiments, a substantial proportion of the progestogen is comprised within the oil droplets of the oil-in-water emulsion. In certain embodiments, in excess of 80% of the progestogen is dissolved and remains within the oil droplets. In certain embodiments greater than 85%, 90%, 92%, 94%, 95%, 96%, 97%, 98%, 99% or 99.5% of the progestogen is dissolved in the oil phase.

3. Aqueous Medium

As noted above, the oil-in-water emulsion compositions of the present invention further comprise an aqueous medium. "Aqueous medium" or "aqueous phase" refers to a water-containing liquid. In some embodiments, the aqueous medium is water and/or an aqueous buffer solution. The compositions according to the "Progestogen/Oil embodiment" may comprise 61.4 to 99.4% wt/vol aqueous medium. The compositions according to the "Phospholipid/Oil embodiment" and the "Progestogen/Oil embodiment" may comprise 80-97% wt/vol, aqueous medium.

In some embodiments, the compositions also may comprise about 0 to 4 mM of a physiologically compatible buffering agent.

4. Emulsifier/Surfactant (Phospholipid)

The compositions of the present invention further comprise one or more emulsifiers/surfactants, including phospholipid. In some embodiments, the emulsifier is of natural origin. Naturally occurring emulsifiers include soy lecithin, egg lecithin, sunflower oil lecithin, sphingosine, gangliosides, phytosphingosine, and combinations thereof. Hydrogenated lecithin, i.e. the product of controlled hydrogenation of lecithin, may also be used in the present invention.

The compositions according to the "Progestogen/Oil embodiment" may comprise 0.0425% to 12.5% wt/vol phospholipid.

The compositions according to both the "Phospholipid/Oil embodiment" and the "Progestogen/Oil embodiment" may comprise 0.085% to 10.2% wt/vol phospholipid, such as 0.11% to 7.65%, including 0.12% to 6.37. % (wt/vol), such as 0.15% to 2.3%. In a more specific embodiment phospholipid may be present within a range (wt/vol) of 0.25% to 2.2%.

Exemplary phospholipids useful in the present invention include, but are not limited to phosphatidyl choline, phosphatidylethanolamine, phosphatidylglycerol, phosphatidic acid, and mixtures thereof. These typically have 4 to about 22 carbon atoms, such as from 10 to 18 carbon atoms, and varying degrees of saturation. The phospholipid component of the compositions can be either a single phospholipid or a mixture of several phospholipids. The phospholipids employed may be natural or synthetic, but should be acceptable for parenteral, especially intravenous, administration.

A non-exhaustive list of suitable phospholipids is listed below: Phosphatidic acids, including 1,2-Dimyristoyl-sn-glycero-3-phosphatidic acid, sodium salt (DMPA,Na), 1,2-Dipalmitoyl-sn-glycero-3-phosphatidic acid, sodium salt (DPPA,Na),1,2-Distearoyl-sn-glycero-3-phosphatidic acid, sodium salt (DSPA,Na); Phosphocholines, including 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Distearoyl-sn-glycero-3-phosphocholine (DSPC) phosphoethanolamines, including 1,2-Dilauroyl-sn-glycero-3-phosphoethanolamine (DLPE),1,2-Dimyristoyl-sn-glycero-3-phosphoethanolamine (DMPE), 1,2-Dipalmitoyl-sn-glycero-3-phosphoethanolamine (DPPE),1,2-Distearoyl-sn-glycero-3-phosphoethanolamine (DSPE); phosphoglycerols including 1,2-Dilauroyl-sn-glycero-3-phosphoglycerol, sodium salt (DLPG, Na), 1,2-Dimyristoyl-sn-glycero-3-phosphoglycerol, sodium salt (DMPG, Na), 1,2-Dimyristoyl-sn-glycero-3-phospho-sn-1-glycerol, ammonium salt (DMP-sn-1-G,NH4), 1,2-Dipalmitoyl-sn-glycero-3-phosphoglycerol, sodium salt (DPPG,Na), 1,2-Distearoyl-sn-glycero-3-phosphoglycerol, sodium salt (DSPG,Na), 1,2-Distearoyl-sn-glycero-3-phospho-sn-1-glycerol, sodium salt (DSP-sn-1G,Na); phosphoserines, including 1,2-Dipalmitoyl-sn-glycero-3-phospho-L-serine, sodium salt (DPPS, Na); mixed chain phospholipids including 1-Palmitoyl-2-oleoyl-sn-glycero-3-phosphocholine (POPC), 1-Palmitoyl-2-oleoyl-sn-glycero-3-phosphoglycerol, sodium salt (POPG, Na), 1-Palmitoyl-2-oleoyl-sn-glycero-3-phosphoglycerol, ammonium salt (POPG,NH4); lysophospholipids, including 1-Palmitoyl-2-lyso-sn-glycero-3-phosphocholine (P-lyso-PC), 1-Stearoyl-2-lyso-sn-glycero-3-phosphocholine (S-lyso-PC); Pegylated Phospholipids, including N-(Carbonyl-methoxypolyethyleneglycol 2000)-MPEG-2000-DPPE, sodium salt, N-(Carbonyl-methoxypolyethyleneglycol 5000)-MPEG-5000-DSPE, sodium salt, N-(Carbonyl-methoxypolyethyleneglycol 5000)-MPEG-5000-DPPE sodium salt, N-(Carbonyl-methoxypolyethyleneglycol 750)-MPEG-750-DSPE, sodium salt, N-(Carbonyl-methoxypolyethyleneglycol 2000)-MPEG-2000-DSPE, sodium salt.

In some embodiments, the amount of phospholipid in the compositions, by weight based on the total volume of the composition (wt/vol), is at least 0.064%, at least 0.1%, at least 0.12%, at least 0.15%, at least 0.25%, or at least 0.5%. In accordance with any of these embodiments, the amount of phospholipid in the compositions, by weight based on the total volume of the composition (wt/vol), is less than or equal to 7.65%, less than or equal to 6.5%, less than or equal to 4.1%, or less than or equal to 3.4%. In more specific embodiments, the amount of phospholipid in the compositions, by weight based on the total volume of the composition (wt/vol), is less than or equal to 3.3%, less than or equal to 2.6%, less than or equal to 2.2%, or less than or equal to 2.1%. In specific embodiments, the compositions comprise phospholipid in an amount (wt/vol) within the range of 0.7% to 2.0%, within the range of 1.0% to 1.3%, or at or about 1.2%. Compositions comprising phospholipid within these limits show excellent physical stability and pH stability throughout storage.

In specific embodiments, the phospholipid component comprises a mixture of phospholipids, such as 79% phosphatidylcholine, 18% phosphatidylethanolamine, 2% sphingomyelin and 1% lysophosphatidylcholine.

In other specific embodiments, the source of the phospholipid emulsifier is lecithin, such as egg lecithin. According to the United States Pharmacopoeia (USP), lecithin is a non-proprietary name describing a complex mixture of acetone-insoluble phospholipids, which consist chiefly of phosphatidylcholine, phosphatidylethanolamine, phosphatidylserine and phosphatidylinositol, combined with various amounts of other substances such as triglycerides, fatty acids, and carbohydrates.

Soy lecithin and egg lecithin (including hydrogenated versions of these compounds) have a long history of safety in biological systems, possess combined emulsification and solubilization properties, and tend to be metabolized in vivo into innocuous substances more rapidly than most synthetic surfactants. Commercially available soya phospholipids/lecithin are the Centrophase and Centrolex products (Central Soya), Phospholipon (Phospholipid GmbH, Germany), Lipoid (Lipoid GmbH, Germany), EPIKURON (Degussa), and PL90 (Fresenius Kabi, Sweden). In specific embodiments, the source of phospholipid is egg lecithin.

In certain embodiments the total amount of emulsifier, including phospholipid in the compositions of the present invention may be within a range of 0.05% to 12%, such as 0.1% to 9% by weight based on the total volume of the composition (wt/vol). In certain embodiments, such as wherein the emulsifier is egg lecithin, the amount of emulsifier (wt/vol) is within a range of 0.15% to 7.6%, such as 0.2% to 6.0%, including 0.3% to 4.8%, such as 0.4% to 3.9%.

In certain embodiments the total amount of emulsifier, including phospholipid, in the compositions is within a range of 0.05% to 15% by weight based on the total volume of the composition (wt/vol). In specific embodiments, the amount of lecithin (wt/vol) is less than or equal to 12%, less than or equal to 9%, less than or equal to 7.6%, less than or equal to 6%, less than or equal to 4.8%, or less than or equal to 3.9%. In certain embodiments, the total amount of lecithin, such as egg lecithin, (wt/vol) is greater than or equal to 0.05%, greater than or equal to 0.13%, greater than or equal to 0.15%, greater than or equal to 0.2%, greater than or equal to 0.3%, or greater than or equal to 0.4%. In specific embodiments, the compositions comprise egg lecithin in an amount (wt/vol) within the range of 0.8% to 2.3%, 0.9% to 1.5%, 1.0% to 1.3%, or preferably 1.2%.

In certain embodiments the total amount of lecithin, especially egg lecithin, (wt/vol) is greater than or equal to 0.05%, greater than or equal to 0.13%, greater than or equal to 0.15%, greater than or equal to 0.2%, greater than or equal to 0.3%, or greater than or equal to 0.4%. In specific embodiments, compositions comprise egg lecithin in an amount (wt/vol) within the range of 0.8% to 2.3%, 0.9% to 1.5%, 1.0% to 1.3%, or at or about 1.2%.

In one embodiment, the emulsifier is egg lecithin comprising 60-80% wt/wt, such as 67% wt/wt phospatidyl choline; 10-20% wt/wt, such as 15% wt/wt, phospatidlylethanolamine; ≦3% wt/wt, such as 2% wt/wt, sphingomyelin; and ≦3% wt/wt, such as 1% wt/wt, lysophosphatidylcholine. "Egg lecithin PL90" (Fresenius Kabi AB) is one example of an egg lecithin having such a phospholipid content.

In one embodiment, the compositions comprise no more than 1.5% wt/wt, no more than 1.2% wt/wt, or no more than 0.8% wt/wt, including no more than 0.4% wt/wt, of polyethylene glycol 15-hydroxystearate. In another embodiment, the compositions comprise no more than 1.5% wt/wt, no more than 1.2% wt/wt, or no more than 0.8% wt/wt, including no more than 0.4% wt/wt, polyethylene glycol ester and/or polyethylene-propylene glycol.

5. Co-Surfactant

In some embodiments, the compositions according to the present invention optionally comprise a co-surfactant. Co-surfactants suitable for use in the compositions of the present invention are those that prevent flocculation and/or coalescence of the oil-in-water emulsion. Exemplary co-surfactants include, but are not limited to cholesterol, oleic acid, oleate, Tween80 (PEG-sorbitan monooleate), HCO-60, Solutol H15 (polyoxyethylene-660-hydroxystearate), PEG-400 (polyethylene glycol), Pluronic F68 (BASF), Cremophor EL (polyoxyethylene-35-ricinoleate), or the salt of a bile acid, such as deoxycholic acid. In other embodiments the co-surfactant is selected from the group consisting of $C_{12}$-$C_{22}$ fatty acids, salts thereof, and/or mixtures thereof, such as from $C_{16}$-$C_{20}$ fatty acids, salts thereof, and/or mixtures thereof; from $C_{18}$ fatty acids, salts thereof, and/or mixtures thereof. In specific embodiments, the fatty acid is mono-unsaturated.

The co-surfactant may be present in compositions of the present invention in an amount between 0.005% and 10% (wt/vol), such as between 0.01% and 5%, including between 0.02% and 0.5% (wt/vol). In other embodiments, the co-surfactant is present in compositions of the present invention in an amount between 0.005% and 4% (wt/vol), such as between 0.01% and 1% (wt/vol), including between 0.02% and 0.04% (wt/vol).

In specific embodiments, the co-surfactant is selected from the group consisting of long-chain fatty acids, such as palmitic acid, oleic acid or stearic acid, or the alkali salts thereof. Oleate and/or oleic acid, particularly sodium oleate, are exemplary suitable co-surfactants.

In certain embodiments, wherein the co-surfactant is oleate and/or oleic acid, the amount of co-surfactant is between 0.005% and 2.5% wt/vol, such as 0.01% and 1.0%, including between 0.02% and 0.5% wt/vol In more specific embodiments, the co-surfactant is sodium oleate and is present in an amount between 0.005 and 0.2% wt/vol, including between 0.01% and 0.2% wt/vol, such as between 0.02% and 0.05% wt/vol In a highly specific example, the co-surfactant is present in an amount of 0.03% wt/vol The compositions described herein may be formulated to be suitable for parenteral infusion, including intravenous infusion, over prolonged periods. A typical duration of administration may be, e.g. 3-7 days. In specific embodiments, the concentration of certain co-surfactants are therefore kept to a minimum to prevent side effects such as irritation, cytochrome P450 inhibition, etc. In some embodiments, Pluronic F68 (poly(ethyleneglycol)-13-poly(propylene glycol co-propylene glycol) is present in an amount less than 0.7% (wt/wt), or less than 0.5% (wt/wt). In other embodiments, Solutol-HS (Macrogol-15-hydroxystearate) is present in an amount less than 1.2% (wt/wt), or less than 1% (wt/wt).

6. Osmotic Agent

In some embodiments, the compositions according to the present invention optionally comprise an osmotic agent and/or a tonicity modulator. As discussed above, the compositions of the present invention may be suitable for parenteral administration, including intravenous administration. Thus, in one embodiment the compositions according to the present invention are isotonic and iso-osmotic. For example, the compositions of the present invention may have an osmolality of 190 mOsm/kg to 1000 mOsm/kg, such as 200 to 1000 mOsm/kg, including 220-600 mOsm/kg such as 230-360 mOsm/kg.

Suitable osmotic and/or tonicity modulating agents include potassium or sodium chloride, trahalose, sucrose, sorbitol, glycerol, glucose, xylitol, mannitol, polyethylene glycol, propylene glycol, albumin, amino acid and mixtures thereof. In certain embodiments, an osmolality of 270 to 330 mOsm/kg, such as 280 to 300 mOsm/kg, is achieved with an agent that also increases osmotic pressure, such as glycerol, dextrose, lactose, and ultimately phase separation sorbitol or sucrose.

In one embodiment, the osmotic agent is a physiologically acceptable polyol, such as glycerol, sorbitol or xylitol. In a specific embodiment, the osmotic agent is glycerol.

The osmotic agent and/or tonicity regulating agent is generally used in an amount that does not have adverse biological effects, but is sufficient to provide iso-osmotic and/or isotonic compositions. When glycerol is the osmotic agent, glycerol may be present in the range of 2 to 5% (wt/vol), such as 2.1% to 2.9% (wt/vol), including 2.3% to 2.7%. In specific embodiments, the emulsions of the present invention comprise 2.5% glycerol.

7. pH Regulating Agent

In some embodiments, the compositions according to the present invention have a pH within the range of pH 6.0 to pH 9.0, such as pH 6.5 to pH 8.5, including pH 7.0 to 8.0. The pH of the compositions may be adjusted by methods known in the art, e.g. through the use of an appropriate base that neutralizes the negative charge on the fatty acids, through the use of an appropriate buffer, or a combination thereof. A variety of bases and buffers are suitable for use with the emulsions of the present invention. One skilled in the art will appreciate that the addition of buffer to the emulsion will affect not only the final pH, but also the ionic strength of the emulsion. High ionic strength buffers may negatively impact the zeta potential of the emulsion and are, therefore, not desirable. In a specific embodiments, the pH is adjusted to the desired value by addition of 1N sodium hydroxide.

8. Optional Additives

The compositions according to the present invention optionally comprise one or more pharmaceutically acceptable additives, such as acidifying, alkalizing, binding, chelating, complexing, solubilizing agents, antiseptics, preservatives (including antimicrobials and antioxidants), suspending agents, stabilizing agents, wetting agents, viscosity modifying agents, solvents, cryo-protectants, diluents, lubricants and other biocompatible materials or therapeutic agents. In certain embodiments, such additives assist in stabilizing the colloidal dispersion or in rendering the formulations of the present invention biocompatible.

In one embodiment, the compositions of the present invention do not comprise Vitamin E. In another embodiment the compositions of the present invention do not comprise Vitamin C. In another embodiment the compositions of the present invention do not comprise hexasodium phytate.

In specific embodiments, the compositions of the present invention are free of, or substantially free of alcohol. In one embodiment, the compositions of the present invention are free of or substantially free of ethanol.

In further embodiments, the compositions of the present invention additionally or alternatively do not contain organic solvents.

In specific embodiments, the compositions according to the "Phospholipid/Oil embodiment" comprise less than 2.5% wt/vol benzyl benzoate.

In specific embodiments, both the compositions according to the "Phospholipid/Oil embodiment" and the compositions according to the "Progestogen/Oil embodiment" may comprise less than 1% wt/vol benzyl benzoate. In more specific embodiments, the compositions comprise less than 1% wt/vol benzyl alcohols and/or derivatives thereof. In specific embodiments, the compositions do not contain benzyl benzoate, and in more specific embodiments, they do not contain benzyl alcohols and/or derivatives thereof. In further specific embodiments, the compositions do not contain cyclodextrin.

Ratios of Composition Components

While exemplary amounts of different components that may be included in the compositions of the invention are set forth above, other aspects of the invention relate to ratios of specific components, as discussed below.

Progestogen:Oil Ratio

As noted above, in some embodiments the compositions of the invention advantageously have a low oil content, such that a minimum amount of oil is delivered to the subject per unit volume, such that adverse side effects such as hyperlipidemia may be avoided. Moreover, in some embodiments, the compositions achieve improved progestogen solubility in oil, whilst maintaining, or improving, the chemical stability and/or physical stability of the emulsions, such that higher doses of progestogen can be delivered to a subject per unit oil.

In specific embodiments, the compositions according to the "Phospholipid/Oil embodiment" have a ratio of progestogen to total oil component (wt/wt) of at least 1:35, at least 1:33, or at least 1:32.

In specific embodiments, the compostions according to the "Phospholipid/Oil embodiment" and the "Progestogen/Oil embodiment" have a ratio of progestogen to total oil component (wt/wt) of greater than 1:32. Advantageously, the ratio of progestogen to total oil component (wt/wt) in the compositions according to the "Phospholipid/oil embodiment" and the "Progestogen/oil embodiment" is at least 1:31. Typically, the latter ratio does not exceed 1:22, or it does not exceed 1:23, 1:24, 1:25, 1:26, 1:27, 1:28, or it does not exceed 1:29 In specific embodiments, the ratio of progestogen to oil component is between 1:32 and 1:25 (wt/wt)), or between 1:31 to 1:29 (wt/wt)).

In specific embodiments, the compositions in accordance with the "Phospholipid/Oil embodiment" comprise progestogen in an amount greater than 2.5% wt/wt of the oil, such as greater than 3% wt/wt of the oil. Both the compositions according to the "Phospholipid/Oil embodiment" and the "Progestogen/Oil embodiment" may comprise progestogen in an amount greater than 3.2% wt/wt of the oil.

Emulsifier (Phospholipid): Oil

It was found that excess amounts of phospholipid in oil-in-water compositions can lead to an increase in phospholipid degradation products following autoclaving and/or storage, causing a drop in pH, which in turn negatively impacts upon emulsion stability. Furthermore, excess phospholipid may lead to an increase in the number of large fat-free micelles in the compositions, and hence an undesirable increase in $PFAT_5$ value. On the other hand, compositions with too low a level of phospholipids do not show sufficient emulsion droplet stability to withstand sterilization by autoclaving and storage. Compositions comprising an optimized amount of phospholipid, relative to the oil content of the composition, demonstrate optimized particle size distribution, excellent physical stability and pH stability throughout storage.

In specific embodiments, the compositions according to the "Progestogen/Oil embodiment" comprise phospholipid in an amount expressed as % wt/wt of the oil, greater than or equal to 6.8% (wt/wt) and less than or equal to 43% (wt/wt).

In specific embodiments, the compositions according to both the "Phospholipid/Oil embodiment", and the "Progestogen/Oil embodiment" comprise phospholipid in an amount expressed as % wt/wt of the oil greater than or equal to 8.4%, greater than or equal to 12%, greater than or equal to 14%, or greater than or equal to 15%. In accordance with any of these embodiments, the compositions may comprise phospholipid in an amount expressed as % wt/wt of the oil of less than or equal to 42.5%, less than or equal to 26%, less than or equal to 25%, or less than or equal to 22%. In very specific embodiments, the phospholipid is present in an amount within the range of 16 to 18% (wt/wt) of the oil.

In other embodiments, the compositions comprise lecithin, such as egg lecithin, in an amount expressed as % wt/wt of the oil, greater than or equal to 8%, greater than or equal to 10%, greater than or equal to 13%, greater than or equal to 15%, or greater than or equal to 18%. In accordance with any of these embodiments, the compositions may comprise lecithin, such as egg lecithin, in an amount expressed as % wt/wt of the oil, of less than or equal to 50%, less than or equal to 48%, less than or equal to 40%, less than or equal to 33%, or less than or equal to 31%. In very specific embodiments, egg lecithin is present in an amount within the range of 19-21% (wt/wt) of the oil.

Co-Surfactant: Oil

As noted above, in certain embodiments of the present invention, the compositions comprise a co-surfactant, such as oleate or oleic acid. In specific embodiments, the co-surfactant is present in an amount expressed as % wt/wt of the oil, of greater than 0.02%, such as greater than or equal to 0.08%, greater than or equal to 0.1%, or greater than or equal to 0.3%. In accordance with any of these embodiments, the concentration of co-surfactant contained in the composition, in an amount expressed as % wt/wt of the oil, may be less than or equal to 2%, less than or equal to 0.9%, or less than or equal to 0.7%. In very specific embodiments, the co-surfactant is oleate or oleic acid, and may be present in an amount of 0.5% of the oil (wt/wt).

Cosurfactant: Emulsifier (Phospholipid)

In one embodiment of the present invention, the compositions comprise phospholipid as an emulsifier, and a co-surfactant, such as oleate. In specific embodiments, the co-surfactant and the phospholipid are present in a co-surfactant to phospholipid ratio (wt/wt) greater than or equal to 1:85, greater than or equal to 1:82, greater than or equal to 1:68, greater than or equal to 1:51, or greater than or equal to 2:85. In accordance with these embodiments the co-surfactant and the phospholipid may be present in a co-surfactant to phospholipid ratio (wt/wt) less than or equal to 1:12, less than or equal to 1:17, less than or equal to 1:20, less than or equal to 1:26, or less than or equal to 1:34. In specific embodiments where the co-surfactant is oleate, the co-surfactant to phospholipid ratio (wt/wt) may be within the range of 1:51 to 1:30, such as 1:51 to 1:34.

In other embodiments, the compositions comprise lecithin and a co-surfactant, such as oleate. In these embodiments, the co-surfactant and the lecithin may present in a co-surfactant to lecithin ratio (wt/wt) greater than or equal to 1:100, greater than or equal to 1:80, greater than or equal to 1:70, greater than or equal to 1:60, or greater than or equal to 1:50. In accordance with these embodiments, the co-surfactant and the lecithin may be present in a ratio (wt/wt) less than or equal to 1:15, less than or equal to 1:20, less than or equal to 3:70, less than or equal to 1:30, or less than or equal to 1:40. In specific embodiments where the co-surfactant is oleate and the lecithin is egg lecithin, the co-surfactant to lecithin ratio (wt/wt) may be within the range of 1:60 to 1:30, or 1:60 to 1:35.

Progestogen: Emulsifier (Phospholipid)

In one embodiment, the progestogen is present in an amount less than 58% wt/wt of the phospholipid, including less than 29% wt/wt of the phospholipid. In accordance with any of these embodiments, the progestogen is progesterone, and the progesterone may be present in amount, expressed as a % wt/wt of the phospholipid, of greater than 7.8%, greater than 9.8%, greater than 13%, or greater than 15%. When the progestogen is progesterone, the progesterone may present in amount, expressed as a % wt/wt of the phospholipid, of less than 47%, less than 39%, less than 26%, or less than 20%.

In specific embodiments, the progestogen is progesterone and phospholipid is lecithin, and the progesterone and lecithin are present in a wt/wt ratio of 1:15 to 2:5, 1:12 to 1:3, 1:9 to 2:9, or 2:15 to 1:6. In specific embodiments, the progesterone to lecithin ratio (wt/wt) is less than 1:2, including less than 1:4.

Progestogen: Co-Surfactant

In one embodiment, co-surfactant is present in compositions according to the present invention in an amount greater than 2.5 wt % of the progestogen, such as than 5% of the progestogen.

Packaging

The compositions of the present invention may be provided as ready-to-use compositions. "Ready-to-use" as used herein means that no further formulation, such as diluting or mixing together of multiple components, is required.

The compositions of the present invention may be provided in sealed packaging. The packaging should be compatible for use with oil-containing formulations and progestogens. Examples of materials not suitable for packaging of oil-containing formulations include PVC and DEHP. Suitable packaging which is compatible with oil-containing formulations includes, but is not limited to, polypropylene-based bags and glass bottles. Conventional glass is a suitable packaging material for compositions of the present invention. In specific embodiments, the composition is packaged in a sealed container. The container may be overwrapped to provide protection from the physical environment. In one embodiment, the composition is packaged in a sealed container having a volume of 250 ml. In one embodiment, the composition is packaged in sealed container under a headspace of inert gas.

In some embodiments the compositions are packaged in inert containers. In some embodiments, the inert containers are light occluded. In other embodiments, the container comprises a double-layered wall, and, in more specific embodiments, the area between the two layers is filled with an inert gas in order to prevent oxidation. For prolonged storage, the packaging material advantageously prevents the diffusion of oxygen from the ambient air towards the compositions of the invention, to prevent the formation of oxygen degradants within the compositions.

In some embodiments, the composition is packaged in a unit dose. A unit dose may provide sufficient composition for administration of a progestogen bolus dose to a subject, or for administration of the composition over a predetermined period of time such as the first hour, first 2 hours, first 4 hours, etc., of treatment. The unit dose enables rapid and convenient administration of the composition in emergency situations, for example by paramedics in the ambulance, or by first aiders/medics at the location an injury/event occurs. Non-limiting examples of unit dose forms are injections, pre-filled syringes, glass vials, and/or sealed bags.

In some embodiments, the composition is packaged within a device similar to an insulin-pump device, which is used to administer a continuous infusion therapy, or in a cartridge designed for use with such a device. Exemplary insulin pumps are those marketed by MiniMed and Disetronic. Such pumps may comprise for example, a cannula, a pump reservoir or cartridge in which the composition is stored, a pump which may be battery operated, and means of allowing the user to control the exact amount of active being delivered, such as for example, a computer chip.

SPECIFIC EXAMPLE

In one specific embodiment, the composition of the present invention comprises 0.13-6.5% wt/vol progesterone; 4-19% wt/vol oil; 0.5-5.7% wt/vol egg lecithin; 70-98.9% wt/vol water; and has a pH of 6.0-9.0. Compositions according to this highly specific embodiment represent a compromise between delivery of the most desirable amount of progestogen per unit volume liquid, delivery of the most desirable amount of progestogen per unit oil, physical stability and safety of administration of the emulsion.

Properties of the Emulsion

Compositions according to the present invention typically are milky white in appearance, and present as visually homogenous emulsions.

Emulsion Droplet Particle Size Distribution $PFAT_5$ Value

The United States Pharmacopeia (USP) sets the limit for globule size distribution in lipid injectable emulsions (USP 729—Pharm. Forum. 2005; 3:1448-1453). The limit for fat globules of diameter>5 µm in injectable emulsions, expressed as volume-weighted percentage fat>5 µm is not exceeding 0.05%, or $PFAT_5$ not exceeding 0.05% (USP 729—Pharm. Forum. 2005; 3:1448-1453). Compositions having a $PFAT_5$, value exceeding 0.05% are considered to be unsafe for intravenous administration. The $PFAT_5$ value of an emulsion may be influenced by several factors including the total oil content of the emulsion, the choice of co-surfactant or surfactant, the surfactant or co-surfactant-to-oil ratio, and the stability of the emulsion droplets to coalescence and/or flocculation.

In specific embodiments, the compositions according to the present invention have a $PFAT_5$ value of less than or equal to 0.05%, such as less than or equal to 0.04%, including less than or equal to 0.02%, such as less than or equal to 0.01%.

In one embodiment, 100% of the emulsion droplets of a composition of the present invention are less than or equal to 5 µm in diameter, and at least 98% of droplets, including 99% of droplets, are less than or equal to 1.5 mm diameter. The particle size distribution of droplets greater than 1 µm in diameter is determined by Coulter counter (Coulter Multisizer III).

PCS

In one embodiment, the droplets less than or equal to 1 mm in diameter have a maximum PCS z-average of 350 nm, and/or a PCS polydispersion value of no more than 0.25. In a specific embodiment, the droplets less than or equal to 1 µm in diameter have a maximum z-average of 250 nm, and/or a polydispersion value of no more than 0.20. In an even more specific embodiment, the droplets less than or equal to 1 µm in size have a maximum z-average of 220 nm, and/or a polydispersion value of no more than 0.15.

Median Droplet Size

The emulsion droplet size is the key parameter determining the kinetics of emulsion destabilisation, since droplet size directly influences the rate of phenomena such as, coalescence, creaming, flocculation, ostwald ripening, and ultimately phase separation. Emulsion droplet size is therefore indicative of emulsion stability. Multiple parameters influence emulsion droplet size, including for example the oil-type, surfactant and co-surfactant type, presence of active ingredients, the amount of oil, oil-to-surfactant and oil-to-co-surfactant ratios.

In one embodiment, the emulsion droplet particles of compositions according to the present invention have a volume-based median diameter, or D[4,3], of $\leq 300$ nm, such as $\leq 230$ nm, including $\leq 200$ nm, such as $\leq 185$ nm, including $\leq 180$ nm.

In a specific embodiment, the compositions according to the present invention maintain a volume-based median diameter, or D[4,3], of $\leq 300$ nm, such as $\leq 230$ nm, including $\leq 200$ nm, such as $\leq 185$ nm, including $\leq 180$ nm, following autoclaving at 121° C. for 15 mins, and/or following storage at 60° C. for at least 3 weeks, including 4 weeks.

Mean Droplet Size

In one embodiment, the emulsion droplet particles of compositions according to the present invention have a volume based mean diameter, or d(0,5) of $\leq 300$ nm, such as $\leq 250$ nm, including $\leq 200$ nm, such as $\leq 185$ nm, including $\leq 180$ nm.

In a specific embodiment, the compositions according to the present invention maintain a volume based mean diameter, or d(0,5) of $\leq 300$ nm, such as $\leq 250$ nm, including $\leq 200$ nm, such as $\leq 185$ nm, including $\leq 180$ nm, following autoclaving at 121° C. for 15 mins, and/or following storage at 60° C. for at least 3 weeks, including 4 weeks.

Span

The Mastersizer "Span" value is a measure of the width or spread of the particle size distribution curve, and is calculated by the formula $d(v,0.9)-d(v,0.1))/d(v,0.5)$ by the Mastersizer unit. In a specific embodiment, compositions of the present invention have a Span of $\leq 2400$ such as $\leq 2100$.

Zeta-Potential

The zeta potential is related to the stability of the emulsion. Emulsions with a high zeta potential are electrically stabilized while those with low zeta potentials tend to coagulate or flocculate. The zeta potential of emulsions is influenced for example by the choice and amount of surfactant and co-surfactant, the pH of the emulsions, as well as ionic strength of the aqueous solution.

In one embodiment, compositions of the present invention have a zeta potential within the range of, −30 mV to −70 mV, such as −40 mV to −65 mV, including −51 mV to −60 mV. In addition, the zeta potential of the emulsion compositions of the present invention may be −30 mV, −35 mV, −40 mV, −45 mV, −50 mV, −55 mV, −60 mV, −65 mV or −70 mV or higher.

Particulate Matter

In certain embodiments the compositions of the present invention are free of crystalline solid at ambient temperature (e.g., at one or more temperatures selected from 4° C., from 2° C. to 8° C. or from 20° C. to 25° C.). In specific embodiments, the emulsion compositions of the present invention meet the standards for particulate size and count in injection liquids (USP 788, Method 2-Microscopic Particle count test). For example, the compositions may contain 0-12 particles per ml equal to or greater than 10 µm, and 0-2 particles per ml equal to or greater than 25 µm.

Stability of the Emulsions

Physical Stability

In specific embodiments, the compositions according to the present invention are surprisingly heat-sterilizable. "Heat-sterilizable" as used herein means that the compositions maintain their physical stability, i.e. do not phase-separate or show signs of flocculation and/or coalescence of the droplets following autoclaving at 121° C. for 15 mins.

In specific embodiments, the compositions according to the present invention are surprisingly storage stable. "Storage stable" as used herein means that the compositions maintain their physical stability, i.e. do not phase-separate or show signs of flocculation and/or coalescence of the droplets following at least three, including four, weeks storage at 60° C. In specific embodiments, the compositions typically do not show any signs of discoloration upon sterilization by autoclaving at 121° C. for 15 min, and/or storage at 60° C. for three or 4 weeks.

In specific embodiments, compositions according to the present invention have a $PFAT_5$ value of less than 0.05%, such as less than or equal to 0.03%, including less than or equal to 0.02%, such as less than or equal to 0.01%, following one, or two, including 3 rounds of autoclaving at 121° C. for 15 mins, and/or following three, or four, weeks storage at 60° C.

In other specific embodiments, the emulsion droplets of compositions according to the present invention show an increase in volume-based mean diameter, or d(0,5), of no greater than 2%, such as no greater than 1.5%, including no greater than 1%, following one, or two, including 3 rounds of autoclaving at 121° C. for 15 mins, and/or following three, or four, weeks storage at 60° C.

In another embodiment, the emulsion droplets of compositions according to the present invention show an increase in volume-based median diameter, or d[4,3], of no greater than 2.5%, such as no greater than 2%, including no greater than 1.5%, following one, or two, including 3 rounds of autoclaving at 121° C. for 15 mins, and/or following three, or four, weeks storage at 60° C.

Chemical Stability

In one embodiment, the progestogen content of compositions according the present invention is not reduced more than 10% by wt progestogen, including not more than 5% by wt progestogen, such as not more than 2% by wt progestogen, following autoclaving at 121° C. for 15 mins, and/or following three, or four, weeks storage at 60° C.

In another embodiment, the amount of progestogen-derived degradation/oxidation products in the compositions of the present invention does not exceed 1% by wt progestogen, or does not exceed 0.7% by wt progestagen for any individual chemical species, and the total sum of progestogen-derived degradation/oxidation products does not exceed 3% by wt progestogen, following autoclaving at 121° C. for 15 mins, and/or following three, or four, weeks storage at 60° C.

In a specific embodiment wherein the progestogen is progesterone, the individual levels of 6-ketoprogesterone, 6-hydroxyprogesterone and 20-hydroxyprogesterone ($\alpha$- and $\beta$-), or $\delta$-6-progesterone do not exceed 1%, or do not exceed 0.7% by wt progesterone, and the total sum of progesterone degradation products does not exceed 3% by wt progesterone, following autoclaving at 121° C. for 15 mins, and/or following three, or four, weeks storage at 60° C.

Progestogen and progestogen degradation/oxidation products may be quantified by HPLC.

Emulsion components themselves are also subject to chemical instability. For example phospholipids are broken down into non-esterified fatty acids (NEFA) during storage. This is especially problematic during heat stress, such as following autoclaving and/or prolonged storage. A build up of NEFA negatively impacts upon the pH of the emulsion and the zeta-potential. For these reasons NEFA levels should be limited in compositions of the present invention.

In another embodiment, the non-esterified fatty acids (NEFA) levels of compositions pre- or post-autoclaving and/or storage following three, or four, weeks at 60° C. is $\leq 12$ mEq/L, specifically less $\leq 8$ mEq/L.

Sterility

In specific embodiments, the compositions according to the present invention are sterile. As used herein "sterile" refers to compositions meeting the requirements of USP Chapter <71>. In specific embodiments the compositions meet the requirements of USP Chapter <85> "Bacterial endotoxin test", and optionally additionally meet the requirements of the USP Chapter <151> "pyrogen test"

In accordance with specific embodiments the compositions according to the present invention advantageously exhibit one or more beneficial characteristics. For example, in accordance with specific embodiments the compositions achieve an improved progesterone to oil ratio, such that less oil is delivered to the subject per unit dose of progestogen, as compared to administration of compositions of the prior art.

In specific embodiments, the compositions of the present invention achieve improved progestogen solubility, whilst maintaining, or improving, the chemical stability and/or physical stability of the emulsions. In specific embodiments, the compositions may be heat-sterilized by autoclaving at 121° C. for 15 minutes without compromising the physical or chemical integrity of the emulsions. Sterilization by autoclaving is beneficial not only in terms of microbiological safety, but also is financially more cost-effective, as compared for example to filter sterilizing.

Furthermore, in some embodiments wherein the compositions have a low oil content (i.e. no greater than 10% wt/vol), a low amount of oil is delivered to the subject per unit volume, such that side effects including hyperlipidemia may be avoided upon administration of the compositions to a subject. In other, high-oil embodiments (i.e. >10% oil), a large amount of progestogen is delivered to the subject per unit volume such that side effects including oedema may be avoided.

Moreover, in specific embodiments, the compositions exhibit safety advantages over the prior art, such as for example, (a) the subject is exposed to less oil per unit dose of active agent, (b) the compositions meet the standards for particle size and count in injection liquids (USP 788, Method 2) and/or comprise a lesser level of progestogen crystals, (c) the compositions have a low $PFAT_5$ value (as discussed in more detail above), (d) the compositions contain lower levels of chemical impurities, (e) the compositions may be autoclaved using the gold standard method for microbiological safety, and/or (f) the compositions do not comprise alcohol or potentially toxic organic solvents.

As a result of one or more of the above-described advantages of the compositions described herein, the compositions provide an improved availability of the progestogen contained therein (e.g., good pharmacokinetics and bioavailability, such as may be reflected in serum hormone levels and/or plasma concentration), and administration of the compositions provides improved consistency in patient dosing, relative to compositions of the prior art.

Finally the emulsion compositions according to the present invention in addition to being convenient and safe to use, are advantageously provided in a sterile, ready-to-use form, have a shelf life of 1 or 2 years at room temperature.

Manufacturing Process

In another aspect, the present invention relates to a method of manufacturing the oil-in-water emulsion compositions as defined herein before, said method comprising the steps of:
a) combining water, and phospholipid, and optionally an osmotic agent to produce an aqueous composition;
b) combining progestogen and oil to produce an oily composition; and
c) combining the aqueous composition and the oily composition followed by homogenization to form a homogenous oil-in-water emulsion.

According to a specific embodiment, the aqueous composition is homogenized so as to produce a homogeneous suspension, before said aqueous composition is combined with the oily composition. In another advantageous embodiment, the progestogen is added to oil having a temperature of at least 40° C. to facilitate dilution of the progestogen. In other specific embodiments, the oily composition is filtered before it is combined with the aqueous composition.

In some very specific embodiments, the methods of manufacture comprise the following steps:
A) dissolving an optional osmotic agent in an aqueous medium and stirring;
B) adding surfactant, such as egg lecithin, and stirring;
C) optionally adding a co-surfactant and optionally a pH regulating agent and mixing;
D) dissolving progestogen in oil to form an oil phase;

E) filtering the oil phase, followed by addition of the filtered oil phase to the aqueous phase, and mixing;
F) homogenization to form a homogenous emulsion;
G) optional addition of water;
H) optional addition of sufficient 1N NaOH to adjust the pH to pH 8.0-8.8;
I) optional addition of sufficient aqueous medium to achieve the final volume.

In specific embodiments, the homogenization is performed at greater than or equal to 350 bar, or greater than or equal to 370 bar.

In specific embodiments, the methods of manufacturing involve the steps of dissolving the egg lecithin in aqueous medium (rather than in oil), adding the oil phase to the aqueous phase (rather than vice versa), and homogenization at greater than or equal to 350 bar. These steps are believed to result in emulsions with advantageous properties in terms of particle size and emulsion stability.

In another specific embodiment, the emulsion is packaged in sealed containers, and sterilized, such as by heating to at least 121° C. (e.g. 121° C. to 123° C.) for a minimum of 15 mins holding time. The autoclave program may be a rotary cycle.

In other very specific embodiments, the methods of manufacture comprise the following steps:
A) dissolving an osmotic agent in an aqueous medium and stirring;
B) adding phospholipid, specifically egg lecithin and stirring;
C) optionally adding a co-surfactant and a pH regulating agent and mixing;
D) dissolving progesterone in soybean oil to form an oil phase
E) filtering the oil phase, followed by addition of the filtered oil phase to the aqueous phase, and mixing.
F) Homogenization to form a homogenous emulsion.
G) Optional addition of water.
H) Optional addition sufficient 1N NaOH to adjust the pH to pH 8.0-8.8.
I) Optional addition of sufficient aqueous medium to achieve the final volume.

The following provides a detailed example of a method of manufacture. The skilled artisan readily will understand that various modifications and variations can be made, and still fall within the scope of the invention.

Preparation of the Pre-Emulsion

A clean vessel (vessel A) is filled to about 15% of the bulk volume with aqueous medium. The temperature of the aqueous medium is adjusted to about 55-60° C. and the aqueous medium is degassed with nitrogen until its residual oxygen content is ≦about 0.1 mg/L. The aqueous medium is kept under a nitrogen atmosphere, with a residual oxygen content of ≦about 0.1 mg/L, throughout the entire duration of the emulsion manufacture process. An osmotic agent is added to the aqueous medium and stirred with a magnetic stirrer for about 3-5 minutes at about 50 Hz. Surfactant (e.g., lecithin) is added to the aqueous mixture. Co-surfactant and a pH regulator are optionally added and the mixture is stirred with a high shear mixer (e.g., UltraTurrax) at about 50 Hz until a homogenous suspension, with no surfactant visible on the surface of the aqueous phase, is obtained.

Oil Phase:

Oil is added to a second vessel (vessel B) and the temperature is adjusted to about 60° C. Progestogen is then dissolved in the heated oil, by stirring with a magnetic stirrer at about 50 Hz for about 10 min+/−5 min.

The oil phase from vessel B is filtered through a 0.2 μm filter and slowly transferred into the aqueous phase in vessel A. The pre-emulsion is obtained by constant stirring at about 50 Hz for about 15 min with a high shear mixer (e.g., Ultra Turrax) until a visually homogenous pre-emulsion is achieved.

Preparation of the Emulsion

The pre-emulsion is subject to about 4 rounds of homogenization. Each round of homogenization comprises a first step wherein the pre-emulsion is subjected to about 400+/−30 bars pressure at a temperature of about 50-80° C. (after heat exchange), and a second step wherein the pre-emulsion is subjected to about 100+/−30 bars pressure at a temperature of about 55-80° C. (after heat exchange).

The emulsion is filtered through a 10 μm filter into a clean storage tank, containing sufficient aqueous medium to give a volume of emulsion equal to about 90% of the final volume. The aqueous medium is degassed with nitrogen until the residual oxygen reaches ≦about 0.1 mg/l, and is maintained under a layer of nitrogen. The emulsion is cooled to about 25-30° C. A pH regulator is optionally added to achieve a pH of 8.0-8.8. Additional aqueous medium may be added to bring the emulsion to the final concentration.

Filling

The emulsion is transferred to a filling machine where it is transferred into packaging and sealed, such as in glass bottles. The filling device is flushed with and stored under nitrogen. A stream of nitrogen is blown into the packaging prior to filling and during the filling process, such that the oxygen content in the packaging remains ≦0.5 mg/L In a specific embodiment, about 255+/−1.5 ml of emulsion is added to each unit of packaging. The filled packages then undergo evacuation. In a specific embodiment, the packages undergo four rounds of air evacuation, each round consisting of 0.5 seconds of air evacuation followed by 0.5 seconds of nitrogen gassing, and a final vacuum value of 0.60 bar (0.40 absolute bar) is achieved. The packages are stoppered, such as with a rubber stopper (e.g. Stelmi RG6720 halobutyle stoppers).

The packaged emulsion is sterilized by autoclaving, for example, within a maximum of about 16 hours holding time (i.e. within about 16 hours post-filling). The autoclaving process typically involves heating to about 121° C. (about 121° C. to about 123° C.) for a minimum of about 15 mins holding time. The autoclave program is, for example, a rotary cycle. Following sterilization the bottles are visually checked for signs of free fat droplets. The emulsion typically is stored at about 15° C. to about 25° C.

Method of Treatment

The compositions described herein may be administered parenterally, such as intravenously or intra-arterially, to subjects for therapeutic or prophylactic use. In specific embodiments the subject is a mammal, such as a human.

The compositions described herein have neuro-protective and/or neuro-regenerative properties. The compositions therefore are useful in the treatment or prevention of nervous system disorders or conditions. Exemplary disorders and conditions include, but are not limited to, central nervous system (CNS) disorders or conditions, spinal chord injury, traumatic brain injury, mild head injury, including concussion characterized by a temporary loss of brain function, pediatric brain injury, degenerative disorders of the CNS such as Parkinson's disease, dementia, including Alzheimer's disease, demyelinating conditions such as multiple sclerosis and chronic, diabetic peripheral neuropathology.

Other exemplary disorders and conditions include ischemic neurological conditions, such as ischemic CNS injury, stroke, including ischemic stroke, hemorrhagic stroke and transient ischemic attacks, and neurocognitive impairments attributed to cardiopulmonary bypass during cardiac surgery, for example post-perfusion syndrome. Further examples include asphasia, sleep disorders, and anxiety disorders such as post-traumatic stress disorder.

The compositions are also useful to provide relief of symptoms associated with the above-listed disorders, such as restoring cognitive function, restoring sleep patterns, normalizing mood disorders, etc. The compositions are also useful to treat post-traumatic stress disorders.

In accordance with one embodiment, the present invention provides methods of treating a mammalian subject with a traumatic CNS injury, such as a traumatic brain injury. Exemplary methods comprise treatment of a TBI in a mammalian subject by administering to the subject in need thereof a pharmaceutical composition according to the present invention, such that a therapeutically effective concentration of progestogen is delivered. In a specific embodiment the mammalian subject is a human. For example, the methods of the present invention may comprise parenterally administering the progestogen-comprising pharmaceutical compositions of the present invention to a subject having a traumatic CNS injury, such as a TBI. In accordance with the method of the present invention, the pharmaceutical composition is used to promote a positive therapeutic response with respect to the traumatic central nervous system injury.

Traumatic brain injury is physical injury to brain tissue that temporarily or permanently impairs brain function. Diagnosis is suspected clinically and may be confirmed by imaging (primarily CT). Clinical manifestations vary markedly in severity and consequences. Injuries are commonly categorized as open or closed. Open injuries involve penetration of the scalp and skull. Closed injuries typically occur when the head is struck, strikes an object, or is shaken violently, causing rapid brain acceleration and deceleration.

The compositions of the invention can be used to treat a TBI, including blunt traumas (e.g., closed traumas), as well as penetrating traumas. By "treatment" is intended any improvement in the subject having the traumatic CNS injury, including both improved morphological recovery (i.e., enhanced tissue viability) and/or behavioral recovery. The improvement can be characterized as an increase in either the rate and/or the extent of behavioral and anatomical recovery following the traumatic CNS injury. Accordingly, a "positive therapeutic response" includes both a complete response and a partial response. Various methods to determine if a complete or a partial therapeutic response has occurred are discussed in detail in patent applications WO2006/102644, WO2006102596, and WO2008/039898.

By "therapeutically effective amount" is meant an amount of progestogen that is sufficient to elicit a therapeutic effect. Thus, in some embodiments, the amount of a progestogen in an administered dose unit in accordance with the present invention is effective in the treatment or prevention of neuronal damage that follows a traumatic injury to the CNS and hence, elicits a neuroprotective effect. Neurodegeneration is the progressive loss of neurons in the central nervous system. As used herein, "neuroprotection" is the arrest and/or reverse of progression of neurodegeneration following a traumatic CNS injury. The therapeutically effective amount will depend on many factors including, for example, the specific activity of the progestogen, the severity and pattern of the traumatic injury, the resulting neuronal damage, the responsiveness of the patient, the weight of the patient, along with other intraperson variability, the mode and/or method of administration, and the progestogen formulation used.

The progestogen emulsion compositions of the present invention may be administered using any acceptable method known in the art, including intravenous (IV) injection, intramuscular (IM) injection, or subcutaneous (SC) injection. In specific embodiments of the invention, the composition is administered intravenously, such as by IV injection. When administered intravenously, the composition can be administered by infusion over a period of from 1 to 144 hours. In some embodiments, infusion of the progestogen occurs over a period of 24 to 72 hours, over a period of 48 to 96 hours, or over a period of 24 to 144 hours. In a specific embodiment, the infusion of the progestogen occurs over a period of 96 to 120 hours.

In one embodiment of the present invention, the composition is administered via parenteral, such as intravenous administration, in a total dose of 0.1 ng to 100 g per kg of body weight, 10 ng to 50 g per kg of body weight, from 100 ng to 1 g per kg of body weight, from 1 µg to 100 mg per kg of body weight, from 1 mg to 90 mg per kg of body weight, from 2 mg to 80 mg per kg of body weight; and from 3 mg to 70 mg per kg of body weight. Alternatively, the amount of progestogen administered to achieve a therapeutic effective dose is 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, or 500 mg per kg of body weight, or greater. In a specific embodiment, progestogen is administered intravenously, in a total dose of between 50 mg and 90 mg per kg of body weight.

Progestogen may be administered once or several times a day. The duration of the treatment may be once per day for a period of 1, 2, 3, 4, 5, 6, 7 days or more. The daily dose can be administered either by a single dose in the form of an individual dosage unit or several smaller dosage units or by multiple administration of subdivided dosages at certain intervals. Subsequent dosage units can be administered any time following the initial administration such that a therapeutic effect is achieved. For instance, additional dosage units can be administered to protect the subject from the secondary wave of edema that may occur over the first several days post-injury. In a specific embodiment, the first dosage unit is administered no later than from 8 hours post-injury.

In specific embodiments of the invention, the progestogen is administered in a constant dosing regimen. By "constant dosing regimen" is meant that the progestogen is administered in a constant total hourly infusion dose of progestogen over the course of treatment. In other embodiments of the invention, the therapy is administered in a "two-level dosing regimen." By "two-level dosing regimen" it is meant that the composition is administered during two dosing time periods. In one embodiment, the total hourly dose of progestogen administered during the first time period of the two-level dosing regimen is a higher total infusion dose of progestogen per hour than that given during the second time period of the two-level dosing regimen. In a specific embodiment, a continuous dose of 0.71 mg/kg/hr is administered intravenously during the first time period of the two-level progestogen dosing regimen, and a dose of 0.5 mg/kg/hr is given during the second time period of the two-level progestogen dosing regimen. In a highly specific embodiment the first time period of the two-level dosing regimen has a duration of 1 hour, and the second time period has a total duration of 120 hours.

The total hourly dose of progestogen to be administered during the constant or two-level progestogen dosing regimen can provide a final serum level of progestogen of 100 ng/ml to 1000 ng/ml, 1100 ng/ml to 1450 ng/ml, 100 ng/ml to 250 ng/ml, 200 ng/ml to 350 ng/ml, 300 ng/ml to 450 ng/ml, 350 ng/ml to 450 ng/ml, 400 ng/ml to 550 ng/ml, 500 ng/ml to 650 ng/ml, 600 ng/ml to 750 ng/ml, 700 ng/ml to 850 ng/ml, 800 ng/ml to 950 ng/ml, 900 ng/ml to 1050 ng/ml, 1000 ng/ml to 1150 ng/ml, 1100 ng/ml to 1250 ng/ml, 1200 ng/ml to 1350 ng/ml, 1300 ng/ml to 1500 ng/m. In specific embodiments, the serum level of progestogen comprises 100 ng/ml, 250 ng/ml, 300 ng/ml, 350 ng/ml, 360 ng/ml, 370 ng/ml, 380 ng/ml, 390 ng/ml, 400 ng/ml, 410 ng/ml, 420 ng/ml, 430 ng/ml, 440 ng/ml, 450 ng/ml, 500 ng/ml, 750 ng/ml, 900 ng/ml, 1200 ng/ml, 1400 ng/ml, or 1600 ng/ml. The serum concentration progestogen can be determined by calculating the area under the curve (AUC) over time following IV administration of the reference composition to a subject, as described in WO2006102596.

In further embodiments of the present invention, at least one additional neuroprotective agent can be administered in combination with the progestogen (either as part of the same composition or in a separate composition) to enhance neuroprotection following a traumatic CNS injury. Such agents include, for example, Vitamin D, and/or compounds that reduce glutamate excitotoxicity and enhance neuronal regeneration, as discussed above. Such agents may be selected from, but not limited to, the group comprising growth factors. By "growth factor" is meant an extracellular signaling molecule that stimulates a cell to grow or proliferate. When the progestogen is administered conjointly with other pharmaceutically active agents, (i.e., other neuroprotective agents) lesser concentrations of progestogen may be therapeutically effective.

Having now generally described this invention, the same will be better understood by reference to certain specific examples which are included herein for purposes of illustration only, and are not intended to be limiting of the invention.

EXAMPLES

Example 1

Highly Desirable Embodiment

The formulation of Example 1 is a 6% oil emulsion composition, comprising 0.2% progesterone and 1.2% egg lecithin. The phospholipid is present in an amount of 17% of the oil (wt/wt), and the progesterone to oil ratio is 1:30 (wt/wt).

TABLE I

| Material | Quantity |
| --- | --- |
| Water for Injection | Ad 400 L |
| Egg lecithin PL90 | 4.77 kg |
| Glycerol | 9.98 kg |
| Oleic acid | 0.12 kg |
| NaOH 1M | 470 ml |
| Soy bean oil | 23.97 kg |
| Progesterone | 0.81 kg |

The emulsion of Table I was manufactured as follows. Components, mixtures and the finished emulsion were kept under nitrogen gas, and at a temperature of 55-60° C., unless otherwise indicated.

180 L of water for injection (w.f.i.) was added to a first vessel, warmed to 58° C., whilst mixing at 50 Hz and degassed with nitrogen until a residual oxygen concentration of ≦0.1 mg/L was obtained. 9.98 kg glycerol (anhydrous Glycerol, Axelis, Austria) was added to the water and mixed for 5 minutes at 50 Hz. 23.97 kg of soybean oil (Fresenius Kabi, Sweden) was added to a second vessel, stirred at 50 Hz and warmed to 58° C. 0.81 kg of progesterone (micronized progesterone by Proquina, Mexico) was added to the heated soybean oil under constant stirring. 4.77 kg egg lecithin (PL90, Fresenius Kabi, Sweden) was added to the warmed water-glycerol mixture, followed by 0.12 kg oleic acid (Merck KGaA) and 470 ml NaOH 1M (Merck KGaA). The contents of the first vessel were stirred with Ultra Torrax (UT) at 50 Hz until a homogenous suspension was obtained (about 15 mins). When the oil phase in the second vessel had reached a temperature of 56° C. and the progesterone was fully dissolved, the mixture was stirred for a further 15 mins. The oil-phase was filtered through a 0.2 mm filter, and slowly transferred into the first vessel (over a period of about 18 mins). Two 5 L volumes of water for injection warmed to 58° C. were used to rinse the second vessel, prior to their addition to the first vessel. An additional 110 mL of NaOH 1M was added to bring the pH to pH8.0. The pre-emulsion was stirred with UT at 50 Hz for 15 minutes and a visually homogenous pre-emulsion was achieved.

The pre-emulsion then underwent 4 rounds of homogenization each round lasting about 70 mins, and each round consisting of 2 homogenization steps. The first round consisted of a first step at 418 bar, and a second step at 108 bar. The second consisted of a first step at 407 bar, and a second step at 103 bar. The third round consisted of a first step at 411 bar, and a second step at 102 bar. The final round consisted of a first step at 410 bar, and a second step at 101 bar. The temperature of the pre-emulsion was between 50° C. and 67° C. inclusive throughout.

150 L w.f.i. was added to a storage tank, heated to 27.9° C. and degassed with Nitrogen gas to reach a residual oxygen concentration of ≦0.1 mg/L. The emulsion was filtered through a 10 μm filter into the w.f.i. containing storage tank. The emulsion was cooled to 27° C., sampled, and sufficient water (23 L) was added to bring the emulsion to final concentration. The final emulsion was degassed to a residual oxygen content of ≦0.1 mg/L, and stored under nitrogen gas at 27° C. for 11 hours prior to filling of the emulsion into bottles. The emulsion was filled into glass bottles, and sealed, giving packaged unit doses of about 250 ml. The amount of oxygen in the emulsion was kept at a level of ≦0.1 mg/L throughout the filling process, by gassing the bottles with nitrogen prior to filling, and gassing the emulsion and the bottles during filling.

The bottles were sterilized by autoclaving on a rotary cycle at 121° C. for a holding time of 15 mins (basket with samples rotating at 4 rpm).

In the following table data is presented on the physical and chemical characteristics of the emulsion of example 1 prior to sterilization, following sterilization by autoclaving at 121° C. for 15 mins, and following storage of the autoclaved emulsion at 60° C. for 3 weeks, and for 4 weeks.

| EXAMPLE 1 | | | | |
|---|---|---|---|---|
| | NON-STERILE | STERILIZED | 3 WEEKS, 60° C. | 4 WEEKS, 60° C. |
| PCS Z-AVERAGE [NM] | 215 | 214 | 217 | 220 |
| PCS POLY | 0.11 | 0.09 | 0.10 | 0.12 |
| MASTERSIZER D[4,3] [µM] | 0.174 | 0.175 | 0.176 | 0.173 |
| MASTERSIZER SPAN | 1.650 | 1.658 | 1.656 | 1.651 |
| MASTERSIZER UNIFORMITY | 0.521 | 0.524 | 0.522 | 0.524 |
| MASTERSIZER d(0,5) [µM] | 0.147 | 0.148 | 0.149 | 0.146 |
| COULTER COUNTER % ≦ 1.5 µM | 99.5 | 99.3 | 100 | 99 |
| COULTER COUNTER % ≦ 5 µM | 100 | 100 | 100 | 100 |
| ACCUSIZER [%] (USP 729) | 0.01 | 0.01 | 0.00 | 0.00 |
| APPEARANCE | WHITE, HOMOGENEOUS | WHITE, HOMOGENEOUS | WHITE, HOMOGENEOUS | WHITE, HOMOGENEOUS |
| PH-VALUE | 8.5 | 7.9 | 6.6 | 7.0 |
| PEROXIDE VALUE [MEQU/L] | 0.01 | 0.04 | 0 | 0.2 |
| NEFA [MEQU/L] | 1 | 2 | 8 | 6 |
| LPC [%] | 1.9 | 2.8 | 16 | 13 |

The emulsions of Example 1 have a particle size distribution representative of stable and safe to administer compositions. The Accusizer values show that the $PFAT_5$ value is well within the limit of <0.05%. The mastersizer data show that the emulsions have low mean (d(0,5)) and median (D[4,3]) particle size values, which are representative of stable emulsions.

Furthermore, the particle size values do not show any significant increases following heat-sterilization or storage at 60° C. for 3 or 4 weeks. The emulsion compositions of Example 1 also exhibit NEFA, LPC and pH values within specification following sterilization and storage.

Comparative Example 2

Progesterone-Containing Oil-in-Water Emulsions

The formulation of Table II is a 20% oil emulsion composition, wherein the phospholipid is present in an amount of 6% of the oil (wt/wt), and the progesterone is present in an amount of 3% of the oil (wt/wt). The 20% emulsion formulation of Table II was further diluted with either saline or water to produce 5% oil emulsions, comprising 0.26% phospholipid and 0.15% progesterone. The 5% emulsions produced with saline are non-homogenous (i.e. they phase-separate), and 5% emulsions produced with water have a very low osmolality. The formulations of example 2 therefore fall outside the scope of the claims of the present invention.

TABLE II

| Material | Per 2000 ml |
|---|---|
| Water for Injection | Ad 2000 ml |
| Egg lecithin | 24 g |
| Glycerol | 50 g |
| Sodium oleate | 0.6 g |
| Soybean oil | 400 g |
| Progesterone | 12 g |

A. The 20% oil emulsion formulation of Table II (Example 2A) was manufactured by the following method. 400 g soybean oil was heated in a vessel to about 70° C. 12 g progesterone was added to the soybean oil and the mixture was stirred using a magnetic stirrer. 400 ml water was placed in a separate vessel and heated to about 70° C. 50 g glycerol was added to the water phase and dissolved by high shear mixing. 24 g egg lecithin was added to the glycerol solution under high shear mixing. The oil phase was slowly added to the aqueous phase under constant high shear mixing. 0.6 g sodium oleate was added and the solution was further mixed. The resultant pre-emulsion underwent 4 rounds of homogenization at 400 bar (Minilab homogenizer). The emulsion was left to cool to 25° C., the final volume was adjusted to 100% (2 L), and the emulsion was stirred. The emulsion was filtered through a 5 µm filter, and filled into 50 ml glass bottles. The bottles were sterilized by autoclaving at 121° C. for a holding time of 15 mins.

B. The 5% oil emulsion of example 2B was made by diluting 500 ml of the non-autoclaved emulsion of Example 2A with 1500 mL 0.9% NaCl. Upon dilution with the 0.9% NaCl, the emulsions phase-separated.

C. The emulsion of example 2C was made by diluting 500 ml of the non-autoclaved emulsion of Example 2A with 1500 mL water for injection. The emulsion was filtered through a 5 vim filter. The emulsion was filled into 50 ml glass bottles. The bottles were sterilized by autoclaving at 121° C. for a holding time of 15 mins, and stored for 3 weeks at 60° C.

contains 0.066% Estradiol hemihydrate. The 20% emulsion formulation of Table III was further diluted with either saline or water to produce 5% oil emulsions, comprising

| EXAMPLE 2 | | | | | | |
|---|---|---|---|---|---|---|
| | A NON-STERILE | A STERILIZED | B NON-STERILE | C NON-STERILE | C STERILIZED | C 3 WEEKS, 60° C. |
| Appearance | WHITE, HOMO-GENEOUS | WHITE, HOMO-GENEOUS | PHASE SEPARATED | WHITE, HOMO-GENEOUS | WHITE, HOMO-GENEOUS | WHITE, HOMO-GENEOUS |
| visual control | NO PARTICLES | NO PARTICLES | — | NO PARTICLES | NO PARTICLES | NO PARTICLES |
| PCS Z-Average [nm] | 285.0 | 287.8 | — | 286.7 | 286.2 | 286.0 |
| PCS Poly | 0.10 | 0.12 | — | 0.10 | 0.09 | 0.11 |
| Mastersizer D[4.3] [μm] | 0.348 | 0.355 | — | 0.346 | 0.352 | 0.348 |
| MASTERSIZER SPAN | 1.462 | 1.395 | — | 1.474 | 1.426 | 1.470 |
| MASTERSIZER UNIFORMITY | 0.459 | 0.438 | — | 0.463 | 0.448 | 0.462 |
| MASTERSIZER d(0.5) [μM] | 0.309 | 0.317 | — | 0.307 | 0.313 | 0.308 |
| ACCUSIZER [%] (USP 729) | 0.21 | 0.85 | — | 0.27 | 0.24 | 0.18 |
| PH-VALUE | 8.2 | 7.7 | — | 7.8 | 7.4 | 6.1 |
| OSMOLALITY MOSM | 307 | 307 | 292 | 68 | 68 | 68 |

The 20% emulsion (2A) compositions have a $PFAT_5$ value that exceeds the limits set by USP, chapter <729>. Furthermore, the 20% compositions have larger D[4,3] and d(0,5) values than compositions of the present invention and these values increase upon autoclaving indicating physical instability.

Dilution of 20% oil emulsions of Example 2A with 0.9% NaCl caused the resulting emulsions (2B) to phase-separate. Dilution of the 20% oil emulsions of Example 2A with water to give 5% oil emulsions (2C) gave white homogenous emulsions, with a very low osmolality. Analysis of the physiochemical properties of emulsions 2C revealed that they have a $PFAT_5$ value that far exceeds the maximum value set by USP, chapter <729>. Furthermore, the median particle size and mean particle size values are larger than the equivalent values observed for the emulsions according to the present invention, and they increase upon autoclaving, indicating poor physical stability.

Comparative Example 3

Progesterone- and Estradiol-Containing Oil-in-Water Emulsions

The formulation of Table III is a 20% oil emulsion composition, wherein the phospholipid is present in an amount of 6% of the oil (wt/wt), and the progesterone is present in an amount of 3% of the oil (wt/wt). The formulation additionally 0.26% phospholipid and 0.15% progesterone. The formulations of Example 3 fall outside the scope of the claims of the present invention.

TABLE III

| Material | Per 2000 ml |
|---|---|
| Water for Injection | Ad 2000 ml |
| Egg lecithin | 24 g |
| Glycerol | 50 g |
| Sodium oleate | 0.6 g |
| Soy bean oil | 400 g |
| Progesterone | 12 g |
| Estradiol hemihydrate | 1.32 g |

A. The emulsion of example 3A was manufactured by the following method. 400 g soybean oil was heated in a vessel to 70° C. 12 g progesterone and 1.32 g estradiol hemihydrate were added to the soybean oil. The mixtures were stirred using a magnetic stirrer. 400 ml water was placed in a separate vessel and heated to 70° C. 50 g glycerol was added to the water phase and dissolved by high shear mixing. 24 g egg lecithin was added to the glycerol solution under high shear mixing. The oil phase was slowly added to the aqueous phase under constant high shear mixing. 0.6 g sodium oleate was added and the solution was further mixed. The resultant pre-emulsion underwent 4 rounds of homogenization at 400 bar (Minilab homogenizer). The emulsion was left to cool to 25° C., the final volume was adjusted to 100% (2 L), and the emulsion was stirred. The emulsion was filtered through a 5 µm filter. The emulsion was filled into 50 ml glass bottles. The bottles were sterilized by autoclaving at 121° C. for a holding time of 15 mins.

B. The emulsion of example 3B was manufactured by diluting 500 mL of the non-autoclaved emulsion of Example 2A with 1500 ml 0.9% NaCl and stirring. Upon dilution with the 0.9% NaCl, the emulsions phase-separated.

C. The emulsion of example 3C was manufactured by diluting 500 mL of the non-autoclaved emulsion of Example 3A with 1500 mL water for injection and stirring. The emulsion was filtered through a 5 µm filter. The emulsion was filled into 50 ml glass bottles. Some bottles were sterilized by autoclaving at 121° C. for a holding time of 15 mins, and subsequently stored for 3 or 4 weeks at 60° C.

properties of the emulsions. The 6% oil emulsions of Table IV were prepared by the method outlined below. The emulsions contained 0.2% progesterone, and either 1.8%, 1.5%, 0.9%, or 0.6% lecithin.

TABLE IV

| | EXAMPLE 4 | | | |
|---|---|---|---|---|
| | A | B | C | D |
| Water for Injection | Ad 10 L | Ad 10 L | Ad 10 L | Ad 10 L |
| Egg lecithin | 180 g | 150 g | 90 g | 60 g |
| Glycerol | 250 g | 250 g | 250 g | 250 g |
| Sodium oleate | 3 g | 3 g | 3 g | 3 g |
| Soy bean oil | 600 g | 600 g | 600 g | 600 g |

| | EXAMPLE 3 | | | | | |
|---|---|---|---|---|---|---|
| | A NON-STERILE | A STERILIZED | B Non-Sterile | C Non-Sterile | C STERILIZED | C 3 WEEKS, 60° C. |
| APPEARANCE | WHITE, HOMO-GENEOUS | WHITE, HOMO-GENEOUS | PHASE SEPARATED | WHITE, HOMO-GENEOUS | WHITE, HOMO-GENEOUS | WHITE, HOMO-GENEOUS |
| visual control | NO PARTICLES | NO PARTICLES | — | NO PARTICLES | NO PARTICLES | NO PARTICLES |
| PCS Z-Average [nm] | 281.4 | 287.2 | — | 287.3 | 286.2 | 288.4 |
| PCS Poly | 0.12 | 0.10 | — | 0.10 | 0.11 | 0.13 |
| Mastersizer D[4.3] [µm] | 0.403 | 0.410 | — | 0.419 | 0.404 | 0.401 |
| MASTERSIZER SPAN | 1.757 | 1.704 | — | 1.680 | 1.721 | 1.702 |
| MASTERSIZER UNIFORMITY | 0.652 | 0.634 | — | 0.626 | 0.631 | 0.609 |
| MASTERSIZER d(0.5) [µM] | 0.310 | 0.316 | — | 0.324 | 0.314 | 0.316 |
| ACCUSIZER [%] (USP 729) | 0.80 | 0.71 | — | 0.18 | 0.16 | 0.51 |
| PH-VALUE | 8.3 | 7.8 | — | 8.2 | 7.4 | 6.4 |
| OSMOLALITY MOSM | 394 | 394 | 312 | 75 | 75 | |

The 20% emulsion compositions have a $PFAT_5$ value that exceeds the limits set by USP chapter <729>. Furthermore, the 20% compositions have larger D[4,3] and d(0,5) values than compositions of the present invention and these values increase upon autoclaving indicating physical instability.

Dilution of 20% oil emulsions of Example 3A with 0.9% NaCl, caused the resulting emulsions (3B) to phase-separate. Dilution of the 20% oil emulsions of Example 3A with water to give 5% oil emulsions (3C) gave white homogenous emulsions, with a very low osmolality. Analysis of the physio-chemical properties of emulsions 3C revealed that they have a $PFAT_5$ value that far exceeds the maximum value set by USP chapter <729>. Furthermore, the median particle size and mean particle size values are larger than the equivalent values observed for the emulsions according to the present invention.

Example 4

Effect of Phospholipid

The following example demonstrates the effect of varying the phospholipid content of emulsion compositions on the TABLE IV-continued

| | EXAMPLE 4 | | | |
|---|---|---|---|---|
| | A | B | C | D |
| Progesterone | 20 g | 20 g | 20 g | 20 g |
| NaOH (1M) | 9 ml | 9 ml | 9 ml | 9 ml |
| NaOH (1M) | 3 ml | | | |
| Ad pH 8.0-8.8 | | | | |

The emulsions of example 4A-D were prepared by the following method. 600 g soybean oil (Fresenius Kabi, Sweden) was added to a vessel and warmed to 58° C. The oil was kept under an atmosphere of nitrogen gas whilst 20 g progesterone (micronized progesterone by Proquina, Mexico) was added to the soybean oil and dissolved by mixing with a magnetic stirrer. WFI was placed in a second vessel and heated to 58° C. 250 g glycerol (anhydrous Glycerol, Axelis, Austria) was added to the water phase and dissolved by high shear mixing. The indicated amount of egg lecithin (PL90 by Fresenius Kabi, Sweden) and 3 g sodium oleate (Merck KGaA) were added to the water phase. The oily phase was slowly added to the water phase under constant high shear mixing. 9 ml NaOH was added to the mixture and stirred by high shear mixing. The pre-emulsion underwent four runs of homogenization, each run comprising 2 stages. The first stage of consisting of 400+/−30 bar and the second stage consisting of 100+/−30 bar. The emulsion was cooled to 20° C., sufficient water for injection was added to bring the final volume of the emulsion to 100%, and the emulsion was stirred by high shear mixing. Where necessary, sufficient NaOH (1M) was added to adjust the pH of the emulsion (e.g. Emulsion A: 3 ml NaOH). The emulsion was filtered through a 10 μm filter, and filled into 50 ml glass bottles. The bottles were sterilized on a rotary cycle for 15 min at 121'C. Sterilization was repeated twice. The bottles were subsequently stored for 3 or 4 weeks at 60° C.

| | Example 4A | | | | | |
|---|---|---|---|---|---|---|
| | Non-Sterile | Sterilized 1 x | Sterilized 2 x | Sterilized 3 x | 3 weeks, 60° C. | 4 weeks, 60° C. |
| Appearance | WHITE, HOMOGENEOUS | WHITE, HOMOGENEOUS | WHITE, HOMOGENEOUS | WHITE, HOMOGENEOUS | WHITE, HOMOGENEOUS | WHITE, HOMOGENEOUS |
| VISUAL CONTROL | NO PARTICLES | NO PARTICLES | NO PARTICLES | NO PARTICLES | NO PARTICLES | NO PARTICLES |
| MASTERSIZER D[4.3] [μM] | 0.206 | 0.206 | 0.204 | 0.206 | 0.202 | 0.202 |
| MASTERSIZER SPAN | 1.895 | 1.894 | 1.898 | 1.896 | 1.894 | 1.884 |
| MASTERSIZER UNIFORMITY | 0.585 | 0.585 | 0.587 | 0.586 | 0.586 | 0.583 |
| MASTERSIZER d(0.5) [μM] | 0.169 | 0.168 | 0.167 | 0.168 | 0.165 | 0.165 |
| ACCUSIZER [%] (USP 729) | 0.02 | 0.02 | 0.02 | 0.03 | 0.02 | 0.03 |
| PH-VALUE | 8.0 | 7.7 | 7.5 | 7.4 | 6.6 | 6.9 |

| | Example 4B | | | | | |
|---|---|---|---|---|---|---|
| | Non-sterile | Sterilized 1 X | Sterilized 2 X | Sterilized 3 X | 3 weeks, 60° C. | 4 weeks, 60° C. |
| Appearance | WHITE, HOMOGENEOUS | WHITE, HOMOGENEOUS | WHITE, HOMOGENEOUS | WHITE, HOMOGENEOUS | WHITE, HOMOGENEOUS | WHITE, HOMOGENEOUS |
| VISUAL CONTROL | NO PARTICLES | NO PARTICLES | NO PARTICLES | NO PARTICLES | NO PARTICLES | NO PARTICLES |
| MASTERSIZER D[4.3] [μM] | 0.214 | 0.215 | 0.213 | 0.214 | 0.12 | 0.217 |
| MASTERSIZER SPAN | 1.908 | 1.909 | 1.917 | 1.913 | 1.914 | 1.899 |
| MASTERSIZER UNIFORMITY | 0.587 | 0.587 | 0.590 | 0.589 | 0.590 | 0.583 |
| MASTERSIZER d(0.5) [μM] | 0.176 | 0.176 | 0.174 | 0.175 | 0.174 | 0.179 |
| ACCUSIZER [%] (USP 729) | 0.02 | 0.02 | 0.03 | 0.02 | 0.02 | 0.02 |
| PH-VALUE | 8.3 | 7.9 | 7.6 | 7.4 | 6.4 | 6.5 |

| | Example 4C | | | | | |
|---|---|---|---|---|---|---|
| | Non Sterile | Sterilized 1 X | Sterilized 2 X | Sterilized 3 X | 3 Weeks, 60° C. | 4 Weeks, 60° C. |
| Appearance | WHITE, HOMOGENEOUS | WHITE, HOMOGENEOUS | WHITE, HOMOGENEOUS | WHITE, HOMOGENEOUS | WHITE, HOMOGENEOUS | WHITE, HOMOGENEOUS |
| VISUAL CONTROL | NO PARTICLES | NO PARTICLES | NO PARTICLES | NO PARTICLES | NO PARTICLES | NO PARTICLES |
| MASTERSIZER D[4.3] [μM] | 0.228 | 0.229 | 0.228 | 0.229 | 0.232 | 0.227 |
| MASTERSIZER SPAN | 2.065 | 2.059 | 2.069 | 2.066 | 2.041 | 2.069 |

-continued

Example 4C

| | Non Sterile | Sterilized 1 X | Sterilized 2 X | Sterilized 3 X | 3 Weeks, 60° C. | 4 Weeks, 60° C. |
|---|---|---|---|---|---|---|
| MASTERSIZER UNIFORMITY | 0.633 | 0.632 | 0.635 | 0.635 | 0.628 | 0.637 |
| MASTERSIZER d(0.5) [μM] | 0.181 | 0.182 | 0.180 | 0.182 | 0.185 | 0.80 |
| ACCUSIZER [%] (USP 729) | 0.01 | 0.01 | 0.03 | 0.01 | 0.02 | 0.02 |
| PH-VALUE | 8.2 | 8.0 | 7.8 | 7.6 | 7.2 | 6.8 |

Example 4D

| | Non Sterile | Sterilized 1 x | Sterilized 2 x | Sterilized 3 x | 3 Weeks, 60° C. | 4 Weeks, 60° C. |
|---|---|---|---|---|---|---|
| Appearance | WHITE, HOMO-GENEOUS | WHITE, HOMO-GENEOUS | WHITE, HOMO-GENEOUS | WHITE, HOMO-GENEOUS | WHITE, HOMO-GENEOUS | WHITE, HOMO-GENEOUS |
| VISUAL CONTROL | NO PARTICLES | NO PARTICLES | NO PARTICLES | NO PARTICLES | NO PARTICLES | NO PARTICLES |
| MASTERSIZER D[4,3] [μM] | 0.241 | 0.240 | 0.243 | 0.239 | 0.247 | 0.247 |
| MASTERSIZER SPAN | 2.135 | 2.121 | 2.111 | 2.145 | 2.090 | 2.080 |
| MASTERSIZER UNIFORMITY | 0.658 | 0.654 | 0.652 | 0.660 | 0.646 | 0.644 |
| MASTERSIZER D(0.5) [μM] | 0.189 | 0.189 | 0.192 | 0.187 | 0.196 | 0.196 |
| ACCUSIZER [%] (USP 729) | 0.00 | 0.00 | 0.00 | 0.01 | 0.01 | 0.01 |
| PH-VALUE | 8.1 | 8.1 | 7.8 | 7.7 | 7.7 | 7.4 |

Compositions A-D formed white homogenous emulsions with particle size parameters representative of safe to administer, heat and storage stable emulsions. $PFAT_5$ values are well within the acceptable range ($\leq 0.05\%$). With decreasing lecithin content, a clear trend for increasing span, D[4,3] and d(0,5) values is observed, indicative of decreasing physical stability of the emulsions. In particular a greater increase in particle size (D[4,3], d(0,5)) is observed in the 0.6% lecithin emulsions (formulation 4D) than in the higher lecithin emulsion formulations.

Example 5

Effect of Co-Surfactant

The following example demonstrates how the absence of co-surfactant content of emulsion compositions affects the properties of the emulsions. The 6% oil emulsions of Table V were prepared by the method outlined below.

TABLE V

| Water for Injection | Ad 1 L |
|---|---|
| Egg lecithin | 12 g |
| Glycerol | 25 g |
| Soy bean oil | 60 g |
| Progesterone | 2 g |
| NaOH (1M) Ad pH 8-8.8 | 500 μl |

The emulsion of Example 5 was prepared by the following method. 60 g soybean oil (Fresenius Kabi, Sweden) was added to a vessel and warmed to 72° C. The oil was kept under an atmosphere of nitrogen gas whilst 2 g progesterone (micronized progesterone by Proquina, Mexico) was added to the soybean oil and dissolved by mixing with a magnetic stirrer. WFI was placed in a second vessel and heated to 65° C. 25 g glycerol (anhydrous Glycerol, Axelis, Austria) was added to the water phase and dissolved by high shear mixing. 12 g egg lecithin (PL90 by Fresenius Kabi, Sweden) was added to the water phase. The oily phase was slowly added to the water phase under constant high shear mixing. The pre-emulsion underwent five runs of homogenization, at 600 bar. The emulsion was cooled to 20° C., sufficient water for injection was added to bring the final volume of the emulsion to 100%, and the emulsion was stirred by high shear mixing. 500 μl NaOH was added to the mixture to adjust the pH of the emulsion. The emulsion was filtered through a 10 μm filter, and filled into 50 ml glass bottles. The bottles were sterilized on a rotary cycle for 15 min at 121° C. Sterilization was repeated twice for the samples undergoing stability testing.

| | Non Sterile | Sterilized 1 X | Sterilized 2 X | Sterilized 3 X | 4 Weeks, 60° C. |
|---|---|---|---|---|---|
| | EXAMPLE 5 | | | | |
| Appearance visual control | WHITE, HOMOGENEOUS NO PARTICLES | WHITE, HOMOGENEOUS NO PARTICLES | WHITE, HOMOGENEOUS NO PARTICLES | WHITE, HOMOGENEOUS NO PARTICLES | WHITE, HOMOGENEOUS NO PARTICLES |
| Mastersizer D[4,3] [μm] | 0.228 | 0.228 | 0.220 | 0.225 | 0.227 |
| MASTERSIZER SPAN | 1.911 | 1.893 | 1.934 | 1.902 | 1.893 |
| MASTERSIZER UNIFORMITY | 0.592 | 0.587 | 0.598 | 0.589 | 0.587 |
| MASTERSIZER d(0,5) [μM] | 0.187 | 0.188 | 0.179 | 0.185 | 0.187 |
| ACCUSIZER [%] (USP 729) | 0.06 | 0.06 | 0.02 | 0.04 | 0.03 |
| PH-VALUE | 7.8 | 7.2 | 7.0 | 6.8 | 5.8 |

The co-surfactant free emulsion compositions produced viable emulsions. The particle size parameters D[4,3], d(0,5), Span and $PFAT_5$ values were slightly elevated relative to emulsions containing co-surfactant (Example 1).

Comparative Example 6

TABLE VI

| | |
|---|---|
| Distilled water | Ad 1 L |
| Egg yolk lecithin | 40 g |
| 2.5% glycerine solution (pH adjusted to 8 with NaOH) | 800 ml |
| Soy bean oil | 200 g |
| Progesterone | 4 g |

The 20% oil emulsion of Table VI was prepared by the method outlined below.

200 g soya bean oil, 40 g egg yolk lecithin and 4 g progesterone were uniformly dissolved by heating at approximately 80° C.

The pH of 800 ml of an aqueous solution containing 2.5% of glycerine was adjusted to pH 8 with sodium hydroxide, prior to addition of the aqueous solution to the oil phase. The mixture was heated to about 80° C., and maintained at this temperature and emulsified at 6000 rpm for 30 minutes using an Ultraturrax—T45, in a current of nitrogen.

The mixture was further emulsified, while continuing to maintain the temperature within the range 75° to 85° C., with a Microfluidizer-homogenizer, under the conditions: 4500 psi, 10 passes.

The emulsion was cooled to room temperature and thereafter made up to a total volume of 1000 ml by adding distilled water.

Finally, the emulsion was filtered through an 8 μM Millipore filter.

The resulting emulsion was filled into 50 ml glass bottles. Part of the bottles were sterilized on a rotary cycle for 15 min at 121° C. At the end of the manufacture process, both the sterile and non-sterile emulsions had a white, homogeneous appearance. As can be seen from columns 2 and 5 in the Table below however, the non-sterile and sterile samples were beginning to phase-separate after a few weeks (ca. 11 weeks) of storage at room temperature.

Samples of the sterilized and non-sterilized emulsions were subjected to an accelerated heat test, whereby the emulsions were stored at 60° C. for 4 weeks. Following 2 weeks at 60° C., for the sterilized sample, and following 3 weeks at 60° C., for the non-sterilized sample, the emulsions were however in a very advanced stage of phase separation, i.e. the fat droplets were highly coalesced, such that large volumes of free-fat were visible by naked eye. This means that the emulsions were so non-homogeneous that taking a sample to run a particle size measurement was not possible.

For this reason, the results presented in the Table below only go up to 2 weeks at 60° C. for the non sterile samples and up to 1 week at 60° C. for the sterile samples.

| | Non Sterile After Storage At Room Temp | Non-Sterile 1 Week, 60° C. | Non-Sterile 2 Weeks, 60° C. | Sterilized 1 X, After Storage At Room Temp | Sterilzed 1 X 1 Week, 60° C. |
|---|---|---|---|---|---|
| | EXAMPLE 6 | | | | |
| Appearance | SLIGHTLY BROWN, PHASE SEPARATED | WHITE HOMOGENEOUS | SLIGHT SEPARATION OF THE PHASES AND FREE FAT VISIBLE | SLIGHTLY BROWN, PHASE SEPARATED | FREE FAT VISIBLE |
| visual control | NO PARTICLES | | | NO PARTICLES | |
| PCS Z-average [nm] (S140) | 412 | 477.4 | 482.3 | 676 | 888.5 |
| PCS Poly (S140) | 0.37 | 0.41 | 0.45 | 0.81 | 0.80 |

-continued

EXAMPLE 6

|  | Non Sterile After Storage At Room Temp | Non-Sterile 1 Week, 60° C. | Non-Sterile 2 Weeks, 60° C. | Sterilized 1 X, After Storage At Room Temp | Sterilzed 1 X 1 Week, 60° C. |
| --- | --- | --- | --- | --- | --- |
| Mastersizer D[4,3] [μm] | 0.681 | 0.769 | 0.770 | 1.100 | 1.296 |
| MASTERSIZER SPAN | 1.381 | 1.361 | 1.353 | 1.545 | 1.460 |
| MASTERSIZER UNIFORMITY | 0.424 | 0.419 | 0.417 | 0.475 | 0.441 |
| MASTERSIZER d(0,5) [μM] | 0.619 | 0.704 | 0.705 | 1.020 | 1.217 |
| ACCUSIZER [%] (USP 729) | 0.34 | 0.27 | 1.15 | 1.06 | 3.23 |
| PH-VALUE | 5.1 | 4.7 | 4.5 | 5.0 | 4.5 |

The table above shows that the formulations of Example 6 are not suitable for pharmaceutical use. Firstly, they are not useable after a few weeks storage at room temperature, as can be seen from their appearances and $PFAT_5$ values (0.34% and 1.06% for the non-sterile and sterile samples, respectively). Secondly, the emulsions were so disrupted after 2 and 3 weeks of storage at 60° C. that particle size measurements were not possible. Finally, the accelerated degradation of these samples upon storage at 60° C. is clearly visible from the large increase in $PFAT_5$ values after 1 week (for the sterile sample, 3.23%) and after 2 weeks (for the non-sterile sample, 1.15%). This is to be compared to the values obtained for the emulsions according to the present invention, which remain well below 0.05% after 4 weeks of storage at 60° C. (Example 1).

The invention claimed is:

1. A sterile, ready-to-use, pharmaceutical oil-in water emulsion composition for parenteral administration comprising:
   0.015 to 1.2% wt/vol progestogen;
   0.5-30% wt/vol oil wherein the oil comprises at least 85% wt/wt triglyceride based on the total oil content of the emulsion;
   0.0425-12.5% wt/vol phospholipid;
   61.4-99.4% wt/vol aqueous medium;
   wherein the phospholipid is present in an amount of 6.8%-43% of the oil (wt/wt), and wherein the progestogen is present in an amount greater than or equal to 2.1% wt/wt of the oil.

2. The composition according to claim 1, wherein the progestogen is present in an amount greater than or equal to 2.2% wt/wt of the oil.

3. The composition according to claim 1, wherein the composition contains less than 2.5% wt/vol benzyl benzoate.

4. The composition according to claim 1, wherein the phospholipid is present in an amount within the range of 8.4-42.5% wt/wt of the oil.

5. The composition according to claim 1, wherein the progestogen is present in an amount greater than 2.5% wt/wt of the oil.

6. The composition according to claim 1, wherein said composition contains 0.005-10 wt % of a co-surfactant.

7. The composition according to claim 6, wherein the co-surfactant is selected from oleate, oleic acid and combinations thereof, and is present in the range of 0.005-2.5 wt %.

8. The composition according to claim 1, wherein the progestogen is progesterone.

9. The composition according to claim 1, wherein the composition contains an osmotic agent.

10. The composition according to claim 9, wherein the osmotic agent comprises glycerol.

11. The composition according to claim 1, wherein the composition is suitable for intravenous administration.

12. The composition according claim 1, wherein the composition has an osmolality of between 200 and 1000 mOsm/kg.

13. The compositions according to claim 1, wherein the composition has a $PFAT_5$ value of $\leq 0.05\%$.

14. The composition according to claim 1, wherein the emulsion comprises a dispersed oil phase with droplet particles having a volume-based mean diameter of $\leq 300$ nm.

15. The composition according to claim 14, wherein the droplet particles of the dispersed oil phase have a volume-based mean diameter of $\leq 250$ nm.

16. A method of treatment, comprising administering a composition of claim 1 to a subject in need thereof.

17. The method of claim 16, wherein said subject is human.

18. The method of claim 16, wherein said subject suffers from a traumatic central nervous system injury.

19. A method of manufacturing a composition according to claim 1, comprising:
   (a) combining water, phospholipid and, optionally, an osmotic agent, to produce an aqueous composition;
   (b) combining progestogen and oil to produce an oily composition; and
   (c) combining the aqueous composition and the oily composition, followed by homogenization to form a homogenous oil-in-water emulsion.

20. The method of claim 19, wherein step (c) comprises adding the oily composition to the aqueous composition, and homogenization at greater than or equal to 350 bar.

* * * * *